(12) United States Patent
Selvaraj et al.

(10) Patent No.: US 6,501,004 B1
(45) Date of Patent: Dec. 31, 2002

(54) TRANSGENIC REDUCTION OF SINAPINE IN CRUCIFERA

(75) Inventors: Gopalan Selvaraj, Saskatoon (CA); Ramesh B. Nair, Saskatoon (CA); Richard W. Joy, IV, Alix (CA); Wilfred A. Keller, Saskatoon (CA); Raju S. Datla, Saskatoon (CA)

(73) Assignee: National Research Council of Canada, Ottawa (CA)

( * ) Notice: Subject to any disclaimer, the term of this patent is extended or adjusted under 35 U.S.C. 154(b) by 0 days.

(21) Appl. No.: 09/564,808

(22) Filed: May 5, 2000

Related U.S. Application Data

(60) Provisional application No. 60/132,800, filed on May 6, 1999.

(51) Int. Cl.[7] .................. A01H 5/00; C12N 13/00; C12N 15/00; C12P 21/06; C07H 21/04
(52) U.S. Cl. ............... 800/205; 800/255; 435/172.3; 435/69.1; 435/320.1; 435/415; 435/419; 536/23.6; 536/24.1
(58) Field of Search .................. 435/172.3, 69.1, 435/320.1, 415, 419; 536/23.6, 24.1; 800/205, 255, DIG. 17, DIG. 26

(56) References Cited

U.S. PATENT DOCUMENTS 5,633,436 A * 5/1997 Wandelt ................ 800/205

OTHER PUBLICATIONS

Meyer et al., "Ferrulate–5–hydroxylase from *Arabidopsis thalina* defines a new family of cytochrome P45–dependent monooxygenase", *Proceedings of the National Academy of Sciences*, (1996), vol. 93, pp. 6869–6874.*

* cited by examiner

*Primary Examiner*—W. Gary Jones
*Assistant Examiner*—Arun K. Chakrabarti

(57) ABSTRACT

The sinapine content of seeds of *Brassica napus*, and other crucifera plants, and the resulting seed meal made therefrom, is reduced by transforming cells of the plants to incorporate an expressible exogenous CYP84 monooxygenase enzyme, particularly ferulate 5-hyroxylase (F5H:) enzyme, or an antisense equivalent thereof. This allows for the production of a seed meal that is commercially more valuable. Three specific nucleic acid sequences encoding the F5H polypeptide are disclosed, designated BNF5H1, BNF5H2 and BNF5H3, and genetic constructs produced. The antisense suppression of sinapine is preferred, which can reduce the sinapine content of seed meal by up to 40% compared to wild type or vector-only transformed plants.

21 Claims, 21 Drawing Sheets

```
   1 ataaaaaacatttccagaaaaaagaaaaactaatATGGAGTCTTCTATATCACAAA
  61 CACTAAGCCAAGTAATAGATCCCACCACGCGAAGGCCTCCGTATTCTCATCGTCTCACTTTTCATCT
 121 TCATCGGCCTCATCACACGACGACGAAGGCCTCCGTATCCACCCACGTGGTTAGCCACGTGGTTGGC
 181 CCATCATAGGCAATATGTCAATGATGACCAACTCACCCACCGTGGTTCTCCACATGTACGCCGTTT
 241 CTAAAAAGTACGGTGGCTTGTGCCATCTCCGCATGGATTTCTCCAAGACAGCGTCTTCTCGAACGAC
 301 CATCACCAGACGTGGCTAAACAAGTCCTTCAAGTCCAAGACAGCCGACATGGCGTTTGCTCACT
 361 CAGCTACTATAGCTATAAGCTATTTGACTTATGACCGAGCCGACATGAAGGTGTTTAGCCGTAAAC
 421 ACGGACCGTTTGGAGACAGATGAGGAAAGTTTGCGTCATGAAGGTGTTTAGCCGTAAAC
 481 GAGCCGAGTCGTTGGTCATGGGCCTTCTATCAACGTTGGTGATGAAGTGGACAAATTTTTGCACTGACCCGAAACATAA
 541 GTAACGTTGGTAAGTTCTATCAACGTTCAGCATGTGAAAAGGGACAAGACGAGTTCATACCGTATTCG
 601 CTTACCGGCAGCGTTCGGTCTTAAGCTTTTTGGAGCCCTTCAACGTAGCGGATTTCATACCGTATTCG
 661 TACAAGAGTTCTCTAAGCTTTTTGGAGCCCTTCAACGTAGCGGCTCGTGAAGGCCCGTAATGACCTAGACG
 721 GGTGGATCGATCCTCAAGGAATAAACAAGCGGCTCGTGAAGGAAAGAGAATCAAAACAGTGTTG
 781 GATTATTGACGATATCATCGATGAACACATGAGTTGATGATCTTCTGCTTTTACAGTGAAG
 841 ATGCTGGAGATGTTGTTGATGAGCGAGACAGCGGATCTTCAGAACTCTATCAAACTTACCCGTGACA
 901 AGGCGAAATTAGTGAGCGAGACAGCGGATCTTCAGAACTCTATCAAACTTACCCGTGACA
 961 ATATCAAAGCAATCATCATGACGACGTTATGTTTTGGAGGAACGGTAGCGTCAGCGA
1021 TAGAGTGGGCATTGACTGAATTACTACGGAGCCCCGAGGATCTAAACCGAGTCCAACAAG
1081 AACTCGCTGAAGTCGTCGGACTTGACCGACGTGTGGAAGAATCAGACATCGAGAAGTTGA
1141 CTTTTCTGAAATGCACACTCAAAGAAACCTACACCCGATCCCAAGAAATCTCGCG
1201 TACACGAAACCGCGTTTGCATTGGGCGCGACAAGAACTCTTGGGTTGACCCCGAAACGT
1261 TTATGATCAACGCGTCTAGGTTTTTGCGGGTCGTAGGTCGTCCCCGGGTATGCAACTCGGGTTATACGCGC
1321 TTAGACCGTCTAGGTTTTTGCGGGTCGTAGGTCGTCCCCGGGTATGCAACTCGGGTTATACGCGC
1381 TTATACCATTCGGGTCGCCTGGCCGTAGTATTACATTGCTGTTTGCTTGCACGTGGAAATTACCTGATGGCATGA
1441 TTGAACTAGCCGTCGCCTGGCCGTAGTATTACATTGCTGTTTGCTTGCACGTGGAAATTACCTGATGGCATGA
1501 AACCAAGCGAGCTTGATATGAGCCACGCGCCTTATTTGTTCGTgttttatggttcgaagcacgt
1561 TCTATGCCTGTCCGAGCACGCGCCTTATTTGTTCGTTAAgttatggttcgaagcacgt
1621 ggcgggtgaaggaaaggtggttggtatgttcttgaaagtggtgtgagaagtcaaaaga
1681 agccctgaagatttgtgatgttataataaatatatgttatgttatgtgttcacac
1741 gtgtgttctgatgaaacataaagtggctcttcgtttgtttccaattcttttgtggg
1801 aattcttttcctttgcatgaaacgctgaa aataagatttttttacaactaaa
1861 aaaaaaaaaaaaaaaaa 1880
```

Fig. 3

```
   1 acttccacaaacaatagaaaaaacatttcccagaaaaagaaaactaatATGGAGTCT
  61 TCTATATCACAAACTAAGCCAAGTATTAGATCCCACCAGGGTATTCTCATCGTTGTC
 121 TCACTTTTCATCTTCATCGGCCTCATCACACGCGACGAAGGCTCCGTACCCACCCGT
 181 CCACGTGGTTGGCCCATCATAGGCAATATGTCAATGATGACCAACTCACTCACCGTGGT
 241 TTAGCCAACTTAGCTAAAAGTACGGTGGCCTTGCCATCTCCGCATGGATTTCTCCAC
 301 ATGTACGCCGTTTCCTCGCCAGACGTGGCTAAGCAACTCTATAAGCTATTTGACTTATGACCGAGCCGACATG
 361 TTCTCAAACGACCAGCAACTATAGCTATAAGCTATTTGACTTATTGACCGAGCCGACATG
 421 GCGTTTGCTCACTACGGACCGTTTTGGAGACAGATGAGGAAAGTTTGTGTCATGAAGGTG
 481 TTTAGCCGTAAACGAGCCCAGTCATGGCTTCGTTCGTGATGAAGTGGACAAAATGATC
 541 CGGTCGGTTTCTAGTAACGTTGGTAAGTCTATCAACGTTGGTGAGCAAATTTTGCACTG
 601 ACCCGAAACATAACTTACCGGCAGCAGGGTTCGGGTCAGCATGTGAAAAGGGACAAGACGAG
 661 TTCATAAGAATTTTACAAGAGTTCTCTAAGCTTTTTGGAGCCTTCAACGTAGCCGATTTC
 721 ATACCGTATTTCGGGTGGATCGATCCGCAAGGAATAAACAAGCGGCTCGTGAAGGCCCGT
 781 AATGACCTAGACGGATTTATTGACGATATCATCGATGAACACATAAAGAAGAAAGAGAAT
 841 CAAAACAGTGTTGATGCTGGAGAGCGAAATTAGTGAGCGAGACACGCGATCTTCAGAACTCCATCAAA
 901 TTTTACAGTGAAGAGGCGAAATTAGTGAGCGAGACACGCGATCTTCAGAACTCCATCAAA
 961 CTTACCCGTGACAATATCAAAGCAATCATCATGACGCGTTATGTTTGGAGAACGAAACG
1021 GTAGCGTCAGCGATAGAGTGGGCATTGACTGAGTTATTACGGAGCCCAGAGATCTAAAA
1081 CGAGTCCAACAAGAACTCGCTGAAGTTGTCGGACTTGTCGCACGTGTGAAGAATCAGAC
1141 ATCGAGAAGTTGACTTTTTTGAAATGCACACTCAATGAAACCTAAGGCTACACCCACCG
1201 ATCCCACTCCTCCTCCACGAAACCGAGATCGACGGTTACTTCGTTCCC
1261 AAGAAATCTCGCGTTATGATCAACGCGGTTTGACGCGACAAGAACTCTTCGGTT
1321 GATCCCGAAACGTTTAGACCGTCCAGGTTTTGCGGGTCGTCGTGCCCGGGTATGCAGCTC
1381 AGTAACTTCGAGTTTATACCATTCGGGTCGTGGCCCATATATATTACATTGCTTCACGTGGAAATTA
1441 GGGTTATACGCGCTTGAACTAGCCGTGGCCCATATATTACATTGCTTCACGTGGAAATTA
1501 CCTGATGGCATGAAACCAAGCGAGCTTGATATGAGCGACGCGTGTTTGGTCTGACGGCTCT
1561 AAAGCCACGCGTCTACGCGTCCCGTGCACGCGCCTTATTTGTTCGTTTAAgttatg
1621 Gttcgaaacacgtgccggtgaaatgaaaggtggtggtgatggttcttgaaag
1681 Tggtgtgagaagtcaaacgaagccctgaaaatttgtgatgttatataactatatgtt
1741 Tatgtatttgttgtacacgtacacacgtgttctgatgaaacataaagtggctctt
1801 Tatttcgttttcatctctttgtgggaattttcctgcatgaaatgtaaacgctga
1861 aaataagattttttttacaact 1884
```

Fig. 4

```
   1 ACAAACACTAAGTCAATTATTAGATCCCACAACGGCTATTCTCATCATCGTCTCACTTTT
  61 CATATTCATCGGCCTCATCACACGACGGCGAAGGTCTTACCCACCCGTCCACGTGGTTG
 121 GCCCATCATAGGCAATATGTTAATGATGGACCAACTCACCACCGTGGTTTAGCCAACTT
 181 AGCTAAAAAATATGGCGGCTTGTGCCATCTCCGACAGTCCTCCATGGGCTTCCTCCATATGTATGCCGT
 241 CTCATCACCTCATGTGGCTCGACAAGTCCTCCAAGTCCAAGACAGCATCTTCTCGAACCG
 301 GCCGGCAACGATAGCTATAAGCTATTTGACTTATGACCGAGCGACATGGCGTTCGCTCA
 361 CTACGGACCCGTTTGGAGACAGATGAGGAAAGTGTGTCATGAAGGTGTTTAGCCGTAA
 421 ACGTGCGGAGTCATGGGCTTCTGTTCGAGATGAAGTGGACAAAATTTCGCCCTGACCGTATC
 481 TAGTAACGTTGGTAAGTCTATAAACGTCGGGGAGCAAATTTCGCCCTGACCCGAAACAT
 541 AACTTACCGGGCAGCGTTCGGGTCAGCTTGCGAAAAGGACAAGATGAGTTCATAAGAAT
 601 CTTACAAGAGTTCTCTAAGCTTTTTGGAGCCTTCAACGTAGCAGATTTCATACCATATTT
 661 TGGGTGGATCGATCCACAAGGGATAAGCAAGCGGCTCGTGAAGGCCCGTAATGATCTAGA
 721 CGGATTTATTGACGATATCATCGACGAACATATGGTTGATGATCTTCTGCTTTTACAGTGA
 781 TGATGATGGAGATGTTGGTGATACCGATATGGTTGATGATCTTCTGCTTTTACAGTGA
 841 AGAGGCCAAATTAGTGAGCGAGACAACGGATCTTCAGAATTCTATCAAACTTACCCGTGA
 901 CAATATCAAAGCAATCATCATGGACGTCATGTTCGGAGGAACGAAACGTAGCTTCTGC
 961 AATAGAGTGGGCCTTAACGAGTTATTACGGACTTATTACGGAGCCCCGAGGATCTAAAACGGGTCCAACA
1021 AGAACTCGCTGAAGTTGTCGGACTTGTCGACCGACGTGTGGAAGAATCAGACATCGAGAAGTT
1081 GACTTTTCTGAAATGCACACTCAAAGAACCTAAGGTTACACCCACCGATCCCACTCCT
1141 CCTCCACGAAACCGCAGAGGACACTGAGATCGACGTTACTTCGTTCCCAAGAAATCGCG
1201 CGTTATGATCAACGCGTTTGCCATTGGACGTGACCCTAAATCTTGGCCTGACGCCGAAAC
1261 GTTTAGACCGTCGAGGTTTTAGAACCGGGAGTAGCGGATTTCAAAGGAAGTAACTTCGA
1321 GTTTATACCATTCGGGTCGGGTCGTGCTCATATATTACATGCTTCACATGGAAATTACCTGGGAT
1381 GCTTGAGTTAGCCGTTGCTGACATGAACGACGTGTTTGGTCTGCAGCGCTCCTAAAGCCACTCG
1441 GAAAGCGAGCGAGCTTGACATGAACGACGTGTTTGGTCTGCTGCGCTCCTAAAGCCACTCG
1501 TCTTTTCGCCGTGCCCTAGCACACGCCCTGATTTGTGCTGTC TAA gttatgttcgtagcac
1561 gtggcgggtgtaaaaccaaacgaaggttgtaataggtatgggttcttggaaagagtttg
1621 aaagtcaaatgtagcactgaacatttgtggatgttattatatgtatgtgtatcac
1681 gtgtggtctgatgataaaacataaatggctcttgattttccttttcttttgttgg
1741 gattttccttgaatgaaatgtaactggta aaatata gttttttttatcttaaaaaaa
1801 aaaaaaaaaaaaaaaaaaaaaaaaaaaaaaaaaa 1835
```

Fig. 5

```
  1  MESSISQTLSQVIDPTTGILIVVSLFIFIGLITRRRPPYPPGPRGWPII
 51  GNMSMMDQLTHRGLANLAKKYGGLCHLRMGFLHMYAVSSPDVAKQVLQVQ
101  DSVFSNRPATIAISYLTYDRADMAFAHYGPFWRQMRKVCVMKVFSRKRAE
151  SWASVRDEVDKMIRSVSSNVGKSINVGEQIFALTRNITYRAAFGSACEKG
201  QDEFIRILQEFSKLFEGAFNVADFIPYFGWIDPQGINKRLVKARNDLDGFI
251  DDIIDEHMKKENQNSVDAGDVVDTDMVDDLLAFYSEEAKLVSETADLQN
301  SIKLTRDNIKAIIMDVMFGGTETVASAIEWALTELLRSPEDLNRVQQELA
351  EVVGLDRRVEESDIEKLTFLKCTLKETLRLHPPIPLLHETAEDTEIDGY
401  FVPKKSRVMINAFAIGRDKNSWVDPETFRPSRFLEPGVPDFKGSNFEFIP
451  FGSGRRSCPGMQLGLYALELAVAHILHCFTWKLPDGMKPSELDMSDVFGL
501  TAPKATRLYAVPSTRLICSV 520
```

Fig. 6

```
  1 MESSISQTLSQVLDPTTGILIVVSLFIFIGLITRRRPPYPPGPRGWPII
 51 GNMSMMDQLTHRGLANLAKKYGGLCHLRMGFLHMYAVSSPDVAKQVLQVQ
101 DSVFSNRPATIAISYLTYDRADMAFAHYGPFWRQMRKVCVMKVFSRKRAE
151 SWASVRDEVDKMIRSVSSNVGKSINVGEQIFALTRNITYRAAFGSACEKG
201 QDEFIRILQEFSKLFGAFNVADFIPYFGWIDPQGINKRLVKARNDLDGFI
251 DDIIDEHIKKENQNSVDAGDVVDTDMVDDLLAFYSEEAKLVSETADLQN
301 SIKLTRDNIKAIIMDVMFGGTETVASAIEWALTELLRSPEDLKRVQQELA
351 EVVGLDRRVEESDIEKLTFLKCTLNETLRLHPPIPLLHETAEDTEIDGY
401 FVPKKSRVMINAFAIGRDKNSWVDPETFRPSRFLEPGVPDFKGSNFEFIP
451 FGSGRRSCPGMQLGLYALELAVAHILHCFTWKLPDGMKPSELDMSDVFGL
501 TAPKATRLYAVPCTRLICSV 520
```

Fig. 7

```
  1  QTLSQLLDPTTAILIIVSLFIFIGLITRRRSYPPGPRGWPIIGNMLMMD
 51  QLTHRGLANLAKKYGGLCHLRMGFLHMYAVSSPHVARQVLQVQDSIFSNR
101  PATIAISYLTYDRADMAFAHYGPFWRQMRKVCVMKVFSRKRAESWASVRD
151  EVDKMIRSVSSNVGKSINVGEQIFALTRNITYRAAFGSACEKGQDEFIRI
201  LQEFSKLFGAFNVADFIPYFGWIDPQGISKRLVKARNDLDGFIDDIIDEH
251  MKKKENQNTVDDGDVGDTDMVDDLLAFYSEEAKLVSETTDLQNSIKLTRD
301  NIKAIIMDVMFGGTETVASAIEWALTELLRSPEDLKRVQQELAEVVGLDR
351  RVEESDIEKLTFLKCTLKETLRLHPPIPLLHETAEDTEIDGYFVPKKSR
401  VMINAFAIGRDPKSWPDAETFRPSRFLEPGVADFKGSNFEFIPFGSGRKS
451  CPGMQLGLYALELAVAHILHCFTWKLPDGMKASELDMNDVFGLTAPKATR
501  LFAVPSTRLICAV  513
```

Fig. 8

TRANSGENIC REDUCTION OF SINAPINE IN CRUCIFERA

CROSS-REFERENCE TO RELATED APPLICATION

This application claims the benefit of our prior Provisional application Serial No. 60/132,800, filed on May 6$^{th}$, 1999.

BACKGROUND OF THE INVENTION

1. Field of the Invention

This invention relates to the genetic manipulation of plants of the family Cruciferae (Brassicaceae) to improve the quality and usefulness of seed meal obtained from such plants. More particularly, the invention relates to such genetic manipulation of species of Cruciferae to decrease the content of sinapine in the seeds and seed meal thereof.

2. Background Art

Several species of the family Cruciferae are grown on a commercial scale for the production of oils from the plants seeds. Rape (*Brassica rapa; Brassica napus*) and Canola (*Brassica napus; Brassica rapa*) are examples of such species, among others. The oils extracted from the plant seeds have various uses, e.g. as cooking oils, lubricants and consumable foodstuffs, but the residues of the seeds after oil extraction (referred to as seed meal) also have commercial uses. Canola meal, for example, which forms about 60% of the seed weight and contains about 36–44% crude protein, is primarily used as a protein supplement in animal feeds. However, the use of such seed meals in animal diets is somewhat limited due to presence of several anti-nutritional factors. Among them, sinapine, a major sinapate-derived phenolic ester present in the seeds, imparts a bitter taste to the meal and makes it less palatable to animals (Bell, 1993). The presence of sinapine in the meal also limits its use as a feed supplement for poultry diet as it results in eggs with fishy taint (Bell, 1993).

Sinapine is a metabolic product that accumulates in such seeds supposedly as a reserve seed material and that remains in the solid seed meal after oil extraction. For example, sinapine constitutes 1–4% of dried canola meal. During seed germination, sinapine is hydrolysed (Strack, 1981); however, it is not clear whether sinapine is essential for seed germination and seedling development. Recent identification of an Arabidopsis mutant that fails to accumulate sinapine in seeds but still undergoes normal seed germination, suggests that sinapine is dispensable for seed germination and seedling growth (Chapple et al., 1992). Efforts to develop oil seed (e.g. *B. napus*) breeding lines with low sinapine contents have not been successful, so it would be desirable to produce low-sinapine variants of oilseed species of Cruciferae by other means.

SUMMARY OF THE INVENTION

An object of the invention is to genetically transform plants of the family Cruciferae (Brassicacea), for example *B. napus*, to make the seeds, and particularly the seed meal, thereof more useful and commercially valuable.

Another object of the invention is to reduce the sinapine content of seeds and seed meal of Crucifera plants compared to wild type or vector control plants of the same species.

According to one aspect of the present invention, there is provided a transformed seed-producing plant, or a part thereof, of the Crucifera family containing an exogenous DNA sequence operably linked to a plant promoter for expression of a polypeptide that acts as a CYP84 monooxygenase enzyme, or a polypeptide that is an antisense equivalent of an CYP84 monooxygenase enzyme, or a polypeptide that is a catalytic fragment or derivative of said monooxygenase enzyme or antisense equivalent that does not alter the function of said CYP84 enzyme or antisense equivalent, and which plant or plant part has a reduced content of sinapine in seeds thereof compared to vector control plants or plant parts of the same species lacking said exogenous DNA sequence.

According to another aspect of the invention, there is provided a method of producing a transformed seed-producing plant, or part thereof, of the Crucifera family having a reduced content of sinapine in seeds thereof compared to vector control plants of the same species lacking said exogenous DNA sequence, said method comprising transforming cells of said plant or plant part with an exogenous DNA sequence operably linked to a plant promoter for expression in said plant cell of a polypeptide that acts as a CYP84 monooxygenase enzyme, or a polypeptide that is an antisense equivalent of an CYP84 monooxygenase enzyme, or a polypeptide that is a catalytic fragment or derivative of said monooxygenase enzyme or antisense equivalent, and selecting transformed plants or plant parts having reduced content of sinapine in seeds thereof compared to vector control plants or plant parts of the same species lacking said exogenous DNA sequence.

According to another aspect of the invention, there is provided a seed meal prepared by growing the plant or part thereof as described above, harvesting seeds from the plant, and processing said seeds to form seed meal.

According to another aspect of the invention, there is provided an isolated nucleic acid molecule comprising a nucleotide sequence selected from the group consisting of SEQ ID NO:1, SEQ ID NO:3 or SEQ ID NO:5, or an active fragment, derivative, homolog or analog thereof, or a sequence that is complementary to SEQ ID NO:1, SEQ ID NO:3 or SEQ ID NO:5, or an active fragment thereof, derivative, homolog or analog thereof., or a sequence having at least 90% identity to said sequence or complementary sequence.

According to yet another aspect of the invention, there is provided a chimeric gene causing reduced sinapine content in plant cells of the Crucifera family transformed with the chimeric gene, the chimeric gene comprising: a regulatory nucleotide sequence; and a nucleic acid fragment encoding an active plant CYP84 enzyme; and wherein the nucleic acid fragment is operably linked in either the sense or antisense orientation to the regulatory sequence.

According to yet another aspect of the invention, there is provided a seed meal comprising seeds, or parts thereof, of a transformed seed-producing plant of the Crucifera family containing an exogenous DNA sequence operably linked to a plant promoter for expression of a polypeptide that acts as a CYP84 monooxygenase enzyme, or a polypeptide that is an antisense equivalent of an CYP84 monooxygenase enzyme, or a polypeptide that is a catalytic fragment or derivative of said monooxygenase enzyme or antisense equivalent that does not alter the function of said CYP84 enzyme or antisense equivalent, and which plant or plant part has a reduced content of sinapine in seeds thereof compared to vector control plants or plant parts of the same species lacking said exogenous DNA sequence.

According to a still further aspect of the invention, there is provided a method of producing a transformed seed-producing plant, or part thereof, of the Crucifera family having a reduced content of sinapine in seeds thereof compared to vector control plants of the same species lacking said exogenous DNA sequence, said method comprising transforming cells of said plant or plant part with an exogenous DNA sequence operably linked to a plant promoter for expression in said plant cell of a polypeptide, said DNA sequence being a sequence flanking an endogenous CYP84 gene of the plant, or a sequence that is complementary thereto.

The sequence of the invention preferably expresses an antisense equivalent of a CYP84 monooxygenase or a catalytic fragment or derivative thereof, and the CYP84 monooxygenase is preferably a enzyme capable of hydroxylating coniferaldehyde or ferulate or coniferyl alcohol or other substrates, most preferably derived from B. napus.

The invention also relates to vectors used in the transformation of the plants, and polypeptide sequences produced by expression of the indicated DNA sequences.

The ferulate 5-hyrdoxylase enzyme is currently believed capable of hydroxylating primarily coniferaldehyde and to a lesser extent coniferyl alcohol or ferulic acid or a precursor leading to sinapine. Preferably, the polypeptide what has been referred variously as ferulic acid hydroxylase, ferulate 5-hydroxylase, coniferaldehyde 5-hydroxylase or abbreviated as FAH, F5H, CAld5H or also as CYP84 family of P450 dependent monooxygenase.

The invention also relates to an antibody molecule which binds to the polypeptide of the invention, vectors containing genetic constructs according to the invention, a transgenic Brassica napus plant transformed with the isolated nucleic acid molecule, a transgenic Brassica napus plant transformed with the genetic construct defined above, a seed of Brassica napus transformed with the isolated nucleic acid molecule or the genetic construct and the use of an isolated nucleic acid molecule to reduce the sinapine content of seeds of Brassica napus, and canola meal made from the transformed Brassica napus seeds.

The invention has the advantage that the transformed plants, and progeny thereof, have the ability to produce seeds having a reduced content of sinapine that produces a more valuable and useful seed meal by-product.

BRIEF DESCRIPTION OF THE DRAWINGS

FIG. 3 shows the nucleotide (nt) sequence of BNF5H1 cDNA clone [SEQ ID NO:1]. The coding region is represented in capital letters while the 5' and 3' non-coding region is represented in small letters. The stop codon (TAA) is marked by shaded box while the putative polyadenylation signal (aaataa) is indicated by an open box. An arrow indicates the putative translational start site.

FIG. 4 shows the nucleotide sequence of the BNF5H2 cDNA clone [SEQ ID NO:3]. The coding region is represented in capital letters while the 5' and 3' non-coding region is represented in small letters. The stop codon (TAA) is marked by shaded box while the putative polyadenylation signal (aaataa) is indicated by an open box. An arrow indicates the putative translational start site.

FIG. 5 shows the nucleotide sequence of the BNF5H3 cDNA clone [SEQ ID NO:5]. The coding region is represented in capital letters while the 3'-untranslated region is represented in small letters. The stop codon (TAA) is marked by shaded box while the putative polyadenylation signal (aaatat) is indicated by an open box.

FIG. 6 shows the predicted amino acid sequence of a F5H polypeptide encoded by the BNF5H1 cDNA clone [SEQ ID NO:2].

FIG. 7 shows the predicted amino acid sequence of a F5H polypeptide encoded by the BNF5H2 cDNA clone [SEQ ID NO:4].

FIG. 8 shows the predicted amino acid sequence of a F5H polypeptide encoded by the BNF5H3 cDNA clone [SEQ ID NO:6].

DEFINITIONS

Figure 1:
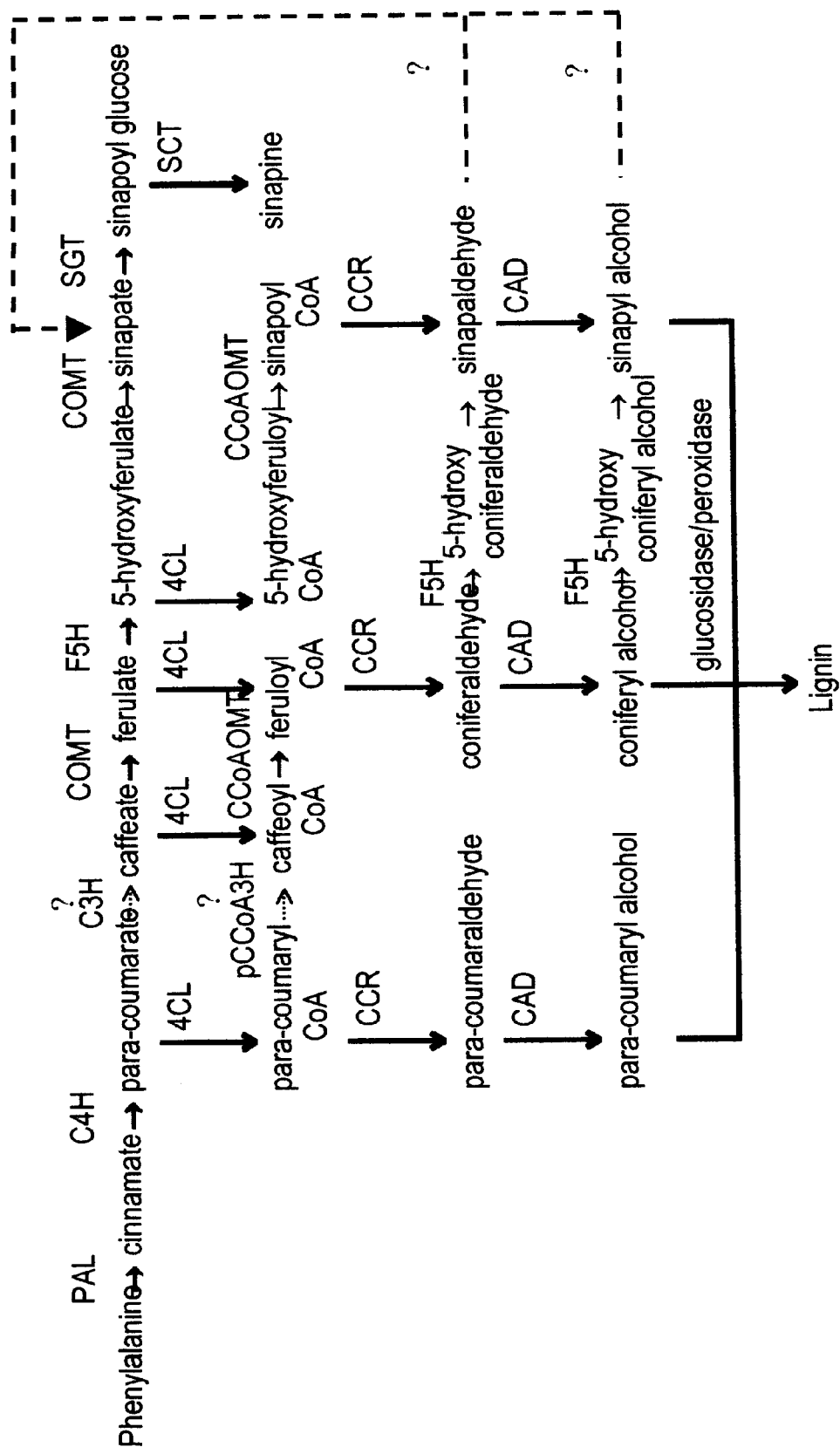
FIG. 1 is a schematic representation of the putative lignin biosynthesis in plants, in which the abbreviations have the following meanings:
PAL: Phenylalanine ammonia lyase;
C4H: Cinnamate 4-hydroxylase;
C3H: Coumarate 3-hydroxylase;
4CL: 4-Coumarate-CoA-ligase;
COMT: Caffeic acid O-methyltransferase
F5H: Ferulic acid 5-hydroxylase; Ferulate 5-hydroxylase;
pCCoA3H: paracoumaryl-CoA 3-hydroxylase
CCoAOMT: Caffeoyl-CoA O-methyltransferase;
CAD: cinnamyl alcohol dehydrogenase;
CCR: cinnamyl CoA reductase;
SGT: sinapate: UDP-glucose sinapoyltransferase; and
SCT: sinapate: choline sinapoyltransferase.
Figure 2:
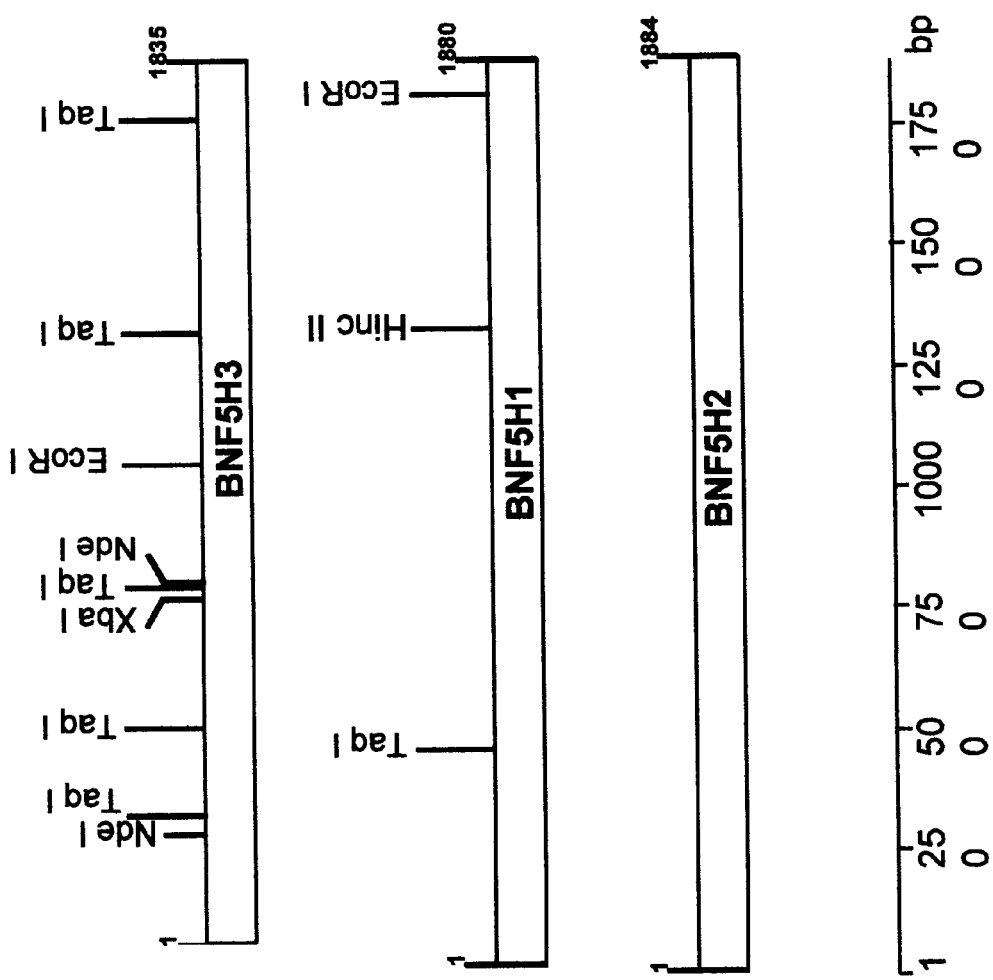
FIG. 2 shows predicted restriction sites that are unique to each of the three F5H cDNA clones according to preferred forms of the invention.

Gene: This term is to be taken in its broadest context and includes: (i) a classical genomic gene consisting of transcriptional and/or translational regulatory sequences and/ or a coding region and/or non-translated sequences (i.e. introns, 5' and 3' untranslated sequences); or (ii) mRNA or cDNA corresponding to the coding regions (i.e. exons) and 5' and 3' untranslated sequences of the gene; or (iii) synthetic or fusion molecules encoding all or part of a functional product.

Chimeric gene: A gene comprising heterologous coding and regulatory sequences.

Exogenous gene: A gene that is additional to the genes found in a genome of a plant.

Endogenous gene: A native gene normally found in its natural location in the genome of a plant.

F5H gene: Any gene which specifically encodes a polypeptide which is a component of a functional enzyme having activity to convert its precursor to its hydroxy form.

BNF5H gene: Any gene directly or indirectly derived from *Brassica napus* which specifically encodes a polypeptide which is a component of a functional enzyme having activity to convert its precursor to its hydroxy form.

Homologue: An homologue of a nucleotide sequence shall be take to refer to an isolated nucleic acid molecule which is substantially the same as a nucleic acid molecule of interest or its complementary nucleotide sequence, notwithstanding the occurrence within that sequence of one or more nucleotide substitutions, insertions, deletions, or rearrangements.

Analogue: An analogue of a nucleotide sequence set forth herein shall be taken to refer to an isolated nucleic acid molecule which is substantially the same as a nucleic acid molecule of interest or its complementary nucleotide sequence, notwithstanding the occurrence of any non-nucleotide constituents not normally present in the isolated nucleic acid molecule, for example, carbohydrates, radiochemicals including radionucleotides, reporter molecules such as, but not limited to, DIG, alkaline phosphatase or horseradish peroxidase, amongst others.

Derivative: A derivative of a nucleotide sequence set forth herein shall be take to refer to any isolated nucleic acid molecule which contains significant sequence similarity to said sequence or part thereof. Generally, the nucleotide sequence of the present invention may be subjected to mutagenesis to produce single or multiple nucleotide substitutions, deletions and/or insertions. Nucleotide insertional derivatives of the nucleotide sequence of the present invention include 5' and 3' terminal fusions as well as intra-sequence insertions of single or multiple nucleotides or nucleotide analogues. Insertional nucleotide sequence variants are those in which one or more nucleotides or nucleotide analogues are introduced into a predetermined site in the nucleotide sequence of said sequence, although random insertion is also possible with suitable screening of the resulting product being performed. Deletional variants are characterized by the removal of one or more nucleotides from the nucleotide sequence. Substitutional nucleotide variants are those in which at least one nucleotide in the sequence has been removed and a different nucleotide or nucleotide analogue inserted in place thereof.

Catalytic fragment: Part of an enzyme that exhibits the enzymatic activity of the entire enzyme, or other designated catalytic effect, and also a part of a DNA sequence that, when translated and expressed, produces an active part of an enzyme as indicated above.

Hybridizing: The ability of a nucleotide molecule to bind to another such molecule under a certain level of stringency.

Stringency: For the purpose of defining levels of stringency, a low stringency is defined herein as being a hybridization and/or wash carried out in 2×SSC–6×SSC buffer, 0.1% (w/v) SDS at 28° C. Generally, the stringency is increased by reducing the concentration of SSC buffer, and/or increasing the concentration of SDS and/or increasing the temperature of the hybridization and/or wash. A medium stringency comprises a hybridization and/or wash carried out in 0.5×SSC–2×SSC buffer, 0.1% (w/v) SDS at 42° C. A high stringency comprises a hybridization and/or wash carried out in 0.1×SSC–0.2×SSC buffer, 0.1% (w/v) SDS at a temperature of at least 55–65° C.

Degree of Similarity or Identity: Sequences are often described as being a certain percentage "identical" to a given sequence. Such degrees of identity or similarity may be determined by carrying out a computer comparison of the respective sequences. All the calculations may be done using a Clustal algorithm with a residue weight table of percent accepted mutations (PAM) 250, for example using the Megalign® program from the Lasergene biocomputing software for windows (DNASTAR Inc., Madison, Wis.) to align sequences.

Under Operable Control of: The nucleic acid molecule of the present invention is generally placed operably under the control of a promoter sequence capable of regulating the expression of the nucleic acid molecule in a prokaryotic or eukaryotic cell, preferably a plant cell. The resulting genetic construct optionally comprises, in addition to a promoter and a sense, or antisense, nucleic acid molecule, a terminator sequence. Placing a nucleic acid molecule under the control of a promoter means positioning the molecule such that expression is controlled by the promoter sequence. Promoters are generally positioned upstream (5') of the genes they control. In the construction of heterologous promoter/structural gene combinations it is generally preferred to position the promoter at a distance from the gene transcription start site that is approximately the same as the distance between the promoter and the gene it controls in its natural setting, i.e. the gene from which the promoter is derived. Some variation of this distance is possible without loss of function, as is well known in the art.

Regulatory Sequences: Nucleotide sequences located upstream (5'), within, or downstream (3') of a coding sequence, which control the transcription and/or expression of the coding sequence in conjunction with the protein biosynthesis apparatus of a cell. The regulatory sequences include promoters, translation leader sequences, transcription termination sequences, and polyadenylation sequences.

Promoter: The transcriptional regulatory sequences of a classical genomic gene, including the TATA box which is required for accurate transcription initiation, with or without a CCAAT box sequence and additional regulatory elements (i.e. upstream activating sequences, enhancers, and silencers) which alter gene expression in response to developmental and/or external stimuli, or in a tissue-specific manner. A promoter is usually, but not necessarily, positioned upstream, or 5'-, of a structural gene, the expression of which it regulates. Furthermore, the regulatory elements comprising a promoter are usually positioned within 2 kb of the start site of transcription of the gene.

Terminator: This is a DNA sequence at the end of a transcriptional unit which signals termination of transcription. The terminators are 3'-non-translated DNA sequences containing a polyadenylation signal, which facilitates the addition of polyadenylate sequences to the 3'-end of a primary transcript. Terminators active in plants are well know in the art and include, but are not limited to, the nopaline synthase (NOS) gene terminator of *Agrobacterium tumefaciens*, the terminator of Cauliflower mosaic virus (CaMV) 35S gene, and the zein gene terminator from *Zea mays*.

Oil seed plant species: These are species of the family Crucifera that are grown commercially for the production of oils from seeds of the plants. Although the seeds of all of substantially all species of Crucifera are capable of producing oil, the commercially grown species have high oil yields (e.g. at least 20%) based on the total seed weight. Commercial oil seed species grown in North America include, but are not necessarily limited to, *Brassica napus, Brassica rapa, Brassica oleracea, Brassica juncea, Brassica nigra* and *Sinapsis alba*. An especially preferred target species for sinapine reduction is *Brassica napus*. This is a two-species-in-one plant comprising *Brassica rapa* and *Brassica oleracea*. Specific reference is made to Kimber, D. S and McGregor, D. I. (Eds,) Brassica Oilseeds: Production and Utilization, Wallingford, Oxon, UK: CAB International, the disclosure of which is incorporated herein by reference.

Seed Meal: This is a product containing whole plant seeds, crushed or broken seeds and/or seed parts that is used primarily as a feed material for animals. The meal contains proteins and carbohydrates at high concentrations (e.g. at least about 20% by weight of the meal, but more preferably at least 25, 30 or 35% by weight of both protein and carbohydrate) but may contain non-nutritive elements, such as sinapine. Seed meal, e.g. canola meal, may be a by-product of a commercial process of oil extraction from plant seeds, when it comprises crushed, compacted and extracted seeds. However, seed meal may be a primary product of plants grown primarily for feedstuff production rather than oil production, in which case the meal may comprise a collection of whole seeds, or seeds that have been crushed, rolled, broken or otherwise treated to make them more digestible in animals and less likely to germinate.

Variation of sinapine content: When the sinapine content of genetically transformed plants or seeds according to the present invention is compared with the sinapine content of wild type, or vector control plants, of the same species or variety, the sinapine content may be expressed in the form of a percentage sinapine reduction or increase. This means that the sinapine content of an average of several (e.g. at least 3) transformed plants is expressed as a percentage of a similar average of a number of plants from the same original wild type or vector control plants grown or transformed essentially at the same time and under the same conditions.

Vector control plants: These are plants or plant cells used as controls in experiments in which other plants of the same species and/or variety have been transformed with a vector containing a nucleotide sequence of interest. The vector control plants have been transformed under the same conditions with the same vector but lacking the gene of interest, so that essentially the only difference between the vector controls and plants under investigation is the presence of the nucleotide sequence of interest and the changes that result therefrom.

DETAILED DESCRIPTION OF THE PREFERRED EMBODIMENTS

The inventors have investigated ways of reducing the sinapine content in species of Crucifera by genetic modification of the phenylpropanoid pathway that eventually leads to the production of lignin and also causes the formation of sinapine as a by-product of secondary metabolism.

As can be seen from the putative phenylpropanoid pathway shown FIG. 1, sinapine is a sinapic acid ester derived from various steps of the general phenylpropanoid pathway. Molecular and biochemical characterization has led to the isolation of several genes that are involved in this pathway (Whetten and Sederoff, 1995). Among the various enzymes that have been characterized, primarily using *Arabidopsis thaliana* as a model, the inventors believe that ferulic acid 5-hydroxylase (F5H) catalyzes the hydroxylation of a compound that functions as a precursor for sinapine synthesis. The enzyme in question has been designated F5H because of an original belief that it catalyzed the conversion of ferulic acid to ferulate 5-hyroxylate, but this possibility was brought into some doubt when Humphreys et al. and Osakabe et al. published papers in 1999 indicating that coniferaldehyde is hydroxylated preferentially. Therefore, the precursor of the enzyme is not precisely known, and is referred to in the following simply as the Precursor. It should also be noted that F5H is sometimes also referred to as FAH for historical reason (Chapple et al., 1991) and lately as CA1d5H (Osakabe et al., 1999), but of course the enzyme remains the same despite the nomenclature adopted by different users. The term F5H will be used exclusively in this application, although this should be construed as including any other nomenclature used for this enzyme.

The inventors of the present invention theorized that, as 5-hydroxyferulic acid or some other metabolite whose synthesis depends at least in part by F5H, may be an intermediate in the formation of sinapine and syringyl lignin, down-regulation of F5H gene expression may reduce the sinapine content. This has been confirmed by experiments carried out with *Brassica napus*.

F5H is a cytochrome P450-linked (dependent) monooxygenase of the CYP84 family. The term CYP84 is a family name assigned to a class of P450-dependent monoxygenases, to which F5H and its relatives belong. There are currently nine members of this family listed on the web site:

http://drnelson.utmem.edu/P450dbplant.html which is the scientific community's nomenclature clearinghouse where the "CYP" numbers are assigned. The current 9 members are listed as follows and further details can be obtained from the web site:

Public 84A Subfamily Members:

84A Subfamily CYP84A1. *Arabidopsis thaliana* GenEMBL U38416 (1838bp) Meyer, K., Cusumano, J. C., Somerville, C. and Chappel, C. C. Ferulate-5-hydroxylase from *Arabidopsis thaliana* defines a new family of cytochrome P450-dependent monoxygenases. Proc. Natl. Acad. Sci. USA 93, 6869–6874 (1996) clone pCC30 Meyer, K., Shirley, A. M., Cusumano, J. C., Bell-Lelong, D. A. and Chapple, C. Lignin monomer composition is determined by the expression of a cytochrome P450-dependent monooxygenase in Arabidopsis PNAS 95, 6619–6623 (1998) functional characterization of CYP84A1.

CYP84A1 *Arabidopsis thaliana* GenEMBL AL022141 F23E13.1 10 (see note to CYP84A3 about function).

CYP84A2 *Solanum lycopersicum* (tomato) (also *Lycopersicon esculentum*) GenEMBL AF150881 G. Paul Bolwell, Jonathan Rees Ferulate-5-Hydroxylase (see note to CYP84A3) 69% identical to 84A1.

CYP84A *Lycopersicon esculentum* (tomato) GenEMBL AI772808 75% identical to 84A1 from amino acids 382–520.

CYP84A *Lycopersicon esculentum* (tomato) GenEMBL AI894552 78% identical to 84A1 from amino acids 297–418.

CYP84A3 *Liquidambar styraciflua* (sweetgum) GenEMBL AF139532 Osakabe, K., Tsao, C. C., Li, L., Popko, J. L., Umezawa, T., Carraway, D. T., Smeltzer, R. H., Joshi, C. P. and Chiang, V. L. Coniferyl aldehyde 5-hydroxylation and methylation direct syringyl lignin biosynthesis in angiosperms Proc. Natl. Acad. Sci. U.S.A. 96, 8955–8960 (1999) 75% identical to CYP84A1 Note: This paper shows coniferyl aldehyde 5-hydroxylation as the primary function of the CYP84A P450s and not ferulate-5-hydroxylation. When both coniferyl aldehyde and ferulate are present, coniferyl aldehyde is a noncompetitive inhibitor of ferulate-5-hydroxylation and shuts down this potential pathway.

CYP84A4 *Populus trichocarpa* cv trichobel GenEMBL AJ010324 Van Doorsselaere, J., Ardiles-Diaz, W., Van Montagu, M. and Boerjan, W. Nucleotide sequence of a cDNA encoding ferulate-5-hydroxylase (f5h) from poplar (*Populus trichocarpa*) Unpublished mRNA for ferulate-5-hydroxylase f5h gene.

*Populus balsamifera* subsp. trichocarpa. 78% identical to 84A3 CYP84A.

*Populus balsamifera* subsp. trichocarpa GenEMBL AI166384 xylem.est.221 94% identical to 84A3.

CYP84A *Glycyrrhiza echinata* (licorice) GenEMBL D89434 Akashi, T., Aoki, T., Takahashi, T., Kameya, N., Nakamura, I. and Ayabe, S. Cloning of cytochrome P450 cDNAs from cultured *Glycyrrhiza echinata* L. cells and their transcriptional activation by elicitor treatment. Plant Science 126, 39–47 (1997) Ge-6 C-terminal PCR fragment.

CYP84A *Glycyrrhiza echinata* (licorice) GenEMBL D89435 Akashi, T., Aoki, T., Takahashi, T., Kameya, N., Nakamura, I. and Ayabe, S. Cloning of cytochrome P450 cDNAs from cultured *Glycyrrhiza echinata* L. cells and their transcriptional activation by elicitor treatment. Plant Science 126, 39–47 (1997) Ge-7 C-terminal PCR fragment CYP84A Glycine max GenEMBL AI495616 78% identical to 84A1 from amino acids 375–516.

CYP84A *Populus tremula* x Populus tremuloides GenEMBL AI166206 81% identical to 84A1 from amino acids 274–368.

While the invention is particularly concerned with the expression of F5H enzymes, the broad form of the invention concerns the expression of all CYP84 enzymes, including those above, in species of Crucifera for the purpose of sinapine reduction. It is believed that all the members of the CYP84 family of monooxygenases are capable of reducing the incorporation of sinapine in Crucifera plants based on the discovered utility of the F5H enzyme for this purpose.

Moreover, while the experiments on which the present invention is based have to date been carried out in *Brassica napus*, there is a very large number of crucifers that are all taxonomically related to *Brassica napus* and that contain sinapine (e.g., as disclosed in Bouchereau et al., 1991) and it is reasonable to expect improvement of these species, as well as *Brassica napus* in accordance with the invention.

Furthermore, while the invention is primarily concerned with introducing expressible CYP84 genes from one specie into plants of the same specie, the invention is believed to be effective for CYP84 genes from one specie introduced into a different specie of the Crucifera family. Indeed, the CYP84 gene may be from a plant or organism that is not of the Crucifera family of plants, provided that the expression of the gene, in the antisense or sense orientation, has the effect of reducing the sinapine content of seeds of the plant.

An *Arabidopsis thaliana* mutant deficient in F5H has been characterized (Chapple et al., 1992) and the gene encoding the enzyme has been isolated from Arabidopsis (Meyer et al., 1996). The use of this gene to transform plants to effect an increase in syringyl monomers, and thus to produce a lignin composition that is more easily degraded by chemicals and enzymes, has been described in U.S. Pat. No. 5,981,837 (the Chapple patent) which issued on Nov. 9, 1999 to Clint Chapple and is assigned to Purdue Research Foundation (the disclosure of which patent is incorporated herein by reference). The Chapple patent is not concerned with the presence or reduction of sinapine in plants of any kind and there is no suggestion that plants transformed with the F5H gene should be selected for low sinapine content, and the sinapine contents of transformed plants are not disclosed.

The inventors of the present invention have now isolated three specific F5H cDNA clones (BNF5H1, -2 and -3) from *Brassica napus* (FIGS. 3, 4 and 5, respectively, and SEQ ID NOs:1, 3 and 5). One of the cDNA clones (BNF5H1) has been used for reducing sinapine content in canola seeds by the down-regulation of F5H gene expression using antisense technique. However, a modest reduction in sinapine content can also be obtained by co-suppression techniques using the cDNA clones expressed in the sense orientation.

In fact, the inventors have identified two groups of F5H genes in *Brassica napus* comprising the genes designated BNF5H1 and BNF5H2 in one group, and BNF5H3 in the other group, but also believe it likely that there is another, very closely related, gene in the BNF5H3 group that may have escaped detection so far. It is believed that this further gene may be detected, isolated and sequenced by the techniques disclosed in the present invention, so this putative additional gene is specifically included in the scope of the present invention.

Figure 9:
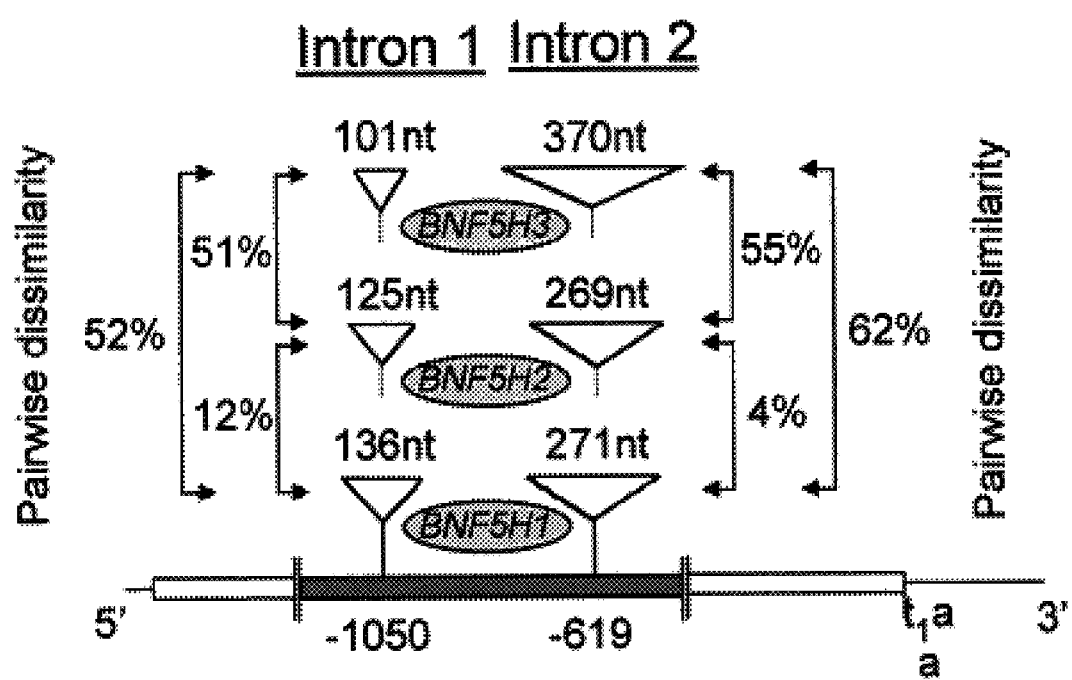
FIG. 9 shows the organizational characteristics of the introns, pertaining to the grouping of the three BNF5H genes. The two introns found in the shaded region corresponding to the cDNA are located at identical points with reference to the stop codon (taa; 1050 nt and 619 nt upstream) in the predicted open reading frame (ORF). The length of the congeneric introns vary as shown. The nt sequence dissimilarity from pairwise comparisons is shown on the left for Intron 1 and on the right for Intron 2. The regions corresponding to the unshaded portions of the ORF have not been examined for the presence of introns.
Figure 10:
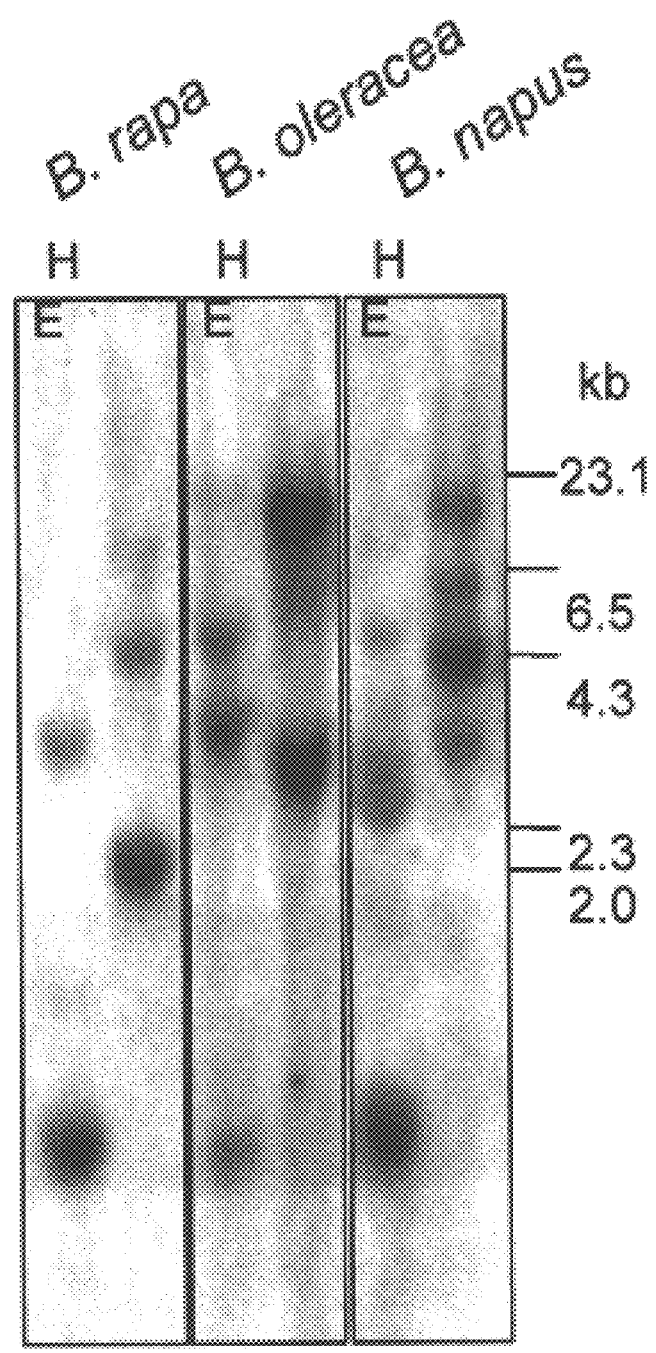
FIG. 10 shows a Southern blot analysis of BNF5H-like sequences in the genomic DNA of the amphidiploid Brassica napus species and its two diploid progenitor representatives. Hind III (H) and EcoR I (E)-digested genomic DNA was probed with a BNF5H1 cDNA fragment (nt 256 to nt 702). Hind III-digested bacteriophage λ DNA size markers in kilo basepairs (kb) are as shown.
Figure 11:
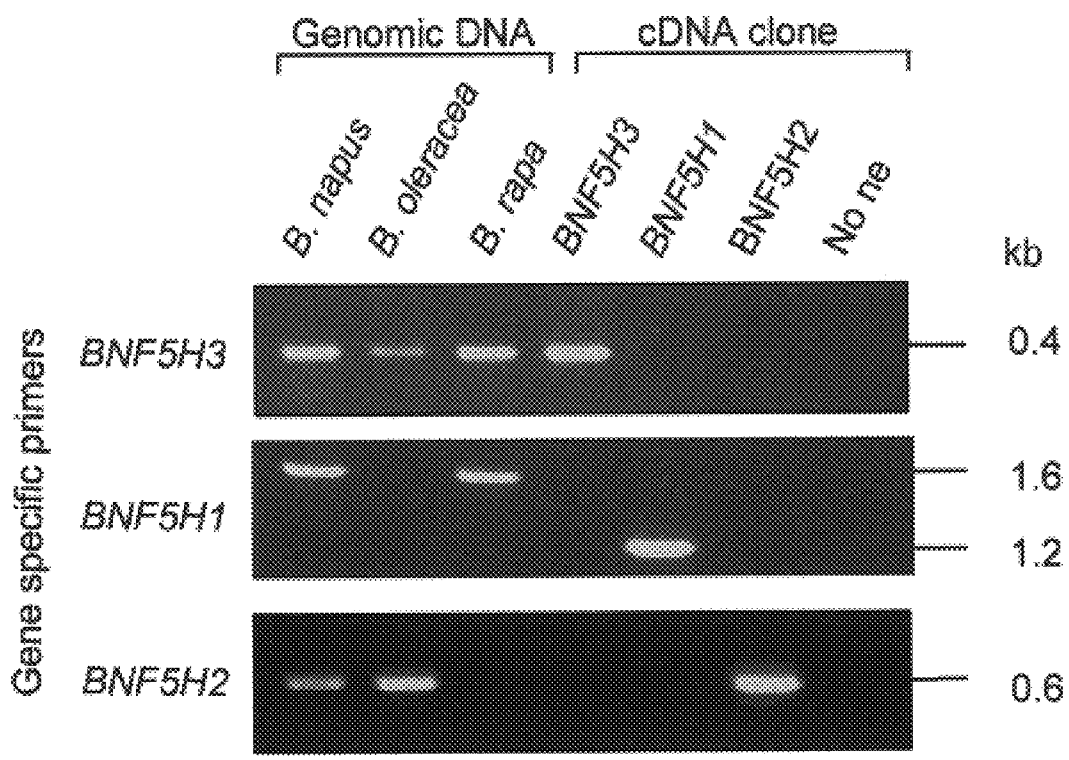
FIG. 11 shows gene-specific amplification of BNF5H sequences from Brassica napus, B. rapa and B. oleracea genomic DNA. The positive controls with the BNF5H cDNAs and negative control with no template DNA are as shown. The BNF5H1-specific primers flank the introns, hence the difference in size between the genomic and cDNA amplicons. The primer sets used here were as follows: Set A for BNF5H1, Set C for BNF5H2 and Set E for BNF5H3 (see later).

The BNF5H genes identified herein add three more members to the CYP84 family, which, as noted above, previously contained the Arabidopsis F5H (Meyer et al., 1996) and subsequently a sweetgum coniferyl aldehyde hydroxylase (Osakabe et al., 1999). The inventors have further shown that the two organizational groups of the *B. napus* CYP84 genes are unlikely to have converged from the hybridization of the two diploid parents (FIGS. 9, 10 and 11). Instead, the two groups must have formed prior to the divergence of *B. oleracea* and *B. rapa*. The greater divergence between BNF5H3 and either of the other two genes suggests that this duplication might have occurred very early in the lineage of the Brassica spp., whose ancestor remains unknown (Truco et al., 1996). A large number of genes exist as families in Brassica spp. In some cases, the gene multiplicity has been attributed in part to the amphidiploid nature of *B. napus* (Slocombe et al., 1994), but the diploids or their ancestor may have undergone a polyploidy event (Kianian and Quiros 1992; Truco et al., 1996; Anderson and Warwick, 1999). The presence of two groups of BNF5H genes in the diploid Brassica spp. might also be due to such polyploidy. The presumptive genetic basis aside, the closer similarity of BNF5H 1 to BNF5H2 (despite their genealogical separation) suggests that the genes got "fixed" for whatever functional requirements. That the gene-specific primers designed for *B. napus* sequences indeed amplified DNA from the cultivars of *B. rapa* and *B. oleracea* chosen at random further illustrates this conservation.

The BNF5H cDNA sequences are the preferred sequences for use in the present invention. However, sequences that differ from the specific sequences are also preferred. According to accepted classification, and any monooxygenases that show more than 40% sequence identity are grouped under the same gene family. Therefore, sequences with at least 40% identity, and more preferably at least 50%, 60%, 70%, 80% or 90% identity with SEQ ID NOs:1, 3 or 5 are preferred for use in the invention. Degrees of identity of more than 90%, and especially more than 95% clearly differentiate the novel sequences of the present invention from previous F5H cDNA sequences from plants other than *B. napus*. The effectiveness of sequences of a certain percentage of identity can be seen by analogy with 4-Coumarate Ligase (4CL) genes, which differ from each other by as much as 35% yet all have 4CL activity. In the case of certain bacterial enzymes compared with their plant counterparts (not 4CL), they may be just 40% identical yet have same enzymatic function (e.g., Boyd L A et al., Gene 103: 45–52, 1991).

Figure 14:
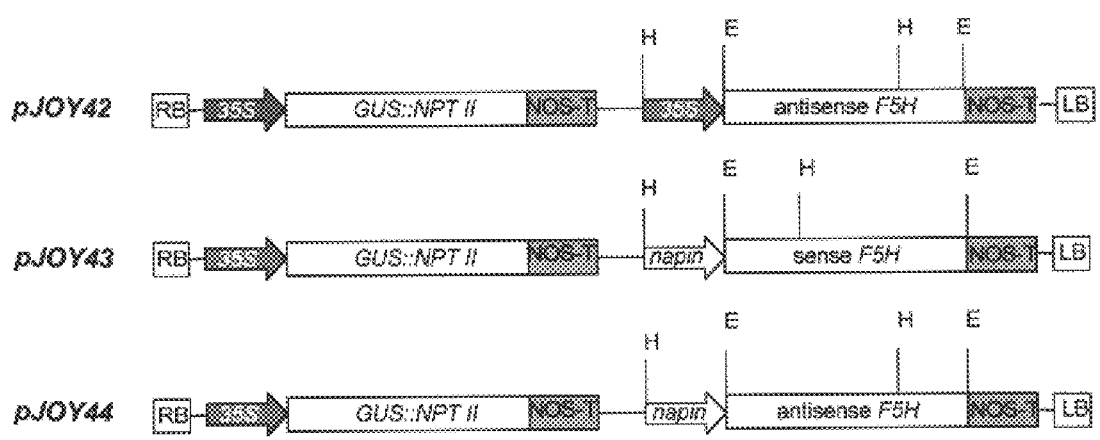
FIG. 14 is a diagrammatic representation of the T-DNA region of the *Agrobacterium tumefaciens* plasmids (pJOY42, pJOY43 and pJOY44) used for the genetic transformation of *Brassica napus*. The following abbreviations are used in the figure: E and H, EcoR I and Hind III restriction endonuclease sites, respectively; RB and LB, The right and left borders, respectively, of the T-DNA. 35S, CaMV35S-AMV leader promoter module from Datla et al. (1993); Napin, the *B. napus* napin promoter from Kohno-Murase et al. (1994). NOS-T, Nopaline synthase terminator region; GUS::NPTII, the bifunctional fusion gene containing β-glucuronidase and neomycin phosphotransferase II (Datla et al., 1991). These plasmids are derivatives of the pHS723 vector that can replicate in *A. tumefaciens* (Hirji et al., 1996). Southern hybridization of Hind III-digested genomic DNA with a GUS probe would estimate the number of T-DNA insertions in the transgenics.

In preferred forms of the present invention, the F5H cDNA clones are preferably used in the antisense orientation to suppress or down-regulate the formation of F5H (FIG. 14). An antisense molecule is an RNA molecule which is transcribed from the complementary strand of a nuclear gene, or (as in the present invention) is a cDNA sequence oriented in a gene construct in reverse order to that which is normally transcribed to produce a "sense" RNA molecule capable of being translated into a polypeptide component of the pathway of interest in the present invention. Therefore, if the identity of a "sense" gene is known, the "antisense" gene can be produced without undue difficulty. An antisense molecule is therefore complementary to the mRNA transcribed from the sense F5H gene or a part thereof Although not limiting the mode of action of the antisense molecules and constructs of the present invention to any specific mechanism, when introduced into a plant having endogenous genes arranged in the "sense" orientation, including monooxygenase genes (such as F5H), and operably linked with a suitable promoter and other transcriptional elements suitable for expression of the genes in plants, the antisense RNA molecule possesses the capacity to form a double-stranded mRNA by base pairing with the sense mRNA, which may prevent translation of the sense mRNA and subsequent synthesis of a polypeptide gene product.

In contrast, co-suppression involves expression of an exogenous gene in the sense orientation (i.e. the order in which the endogenous gene is transcribed) and may cause a reduction in expression of an endogenous gene or prevent the accumulation of polypeptide in a cell that occurs when one or more copies of the gene, or one or more copies of a substantially similar gene, are introduced into the cell. Co-suppression can therefore be brought about by the introduction of an exogenous "sense" gene into a plant having endogenous "sense" copies of the same or similar gene.

Antisense RNA has been used in the past to inhibit plant target genes in a tissue-specific manner (van der Krol et al., Biotechniques 6:958–976 (1988)). Such antisense inhibition has been shown using the entire cDNA sequence as well as a partial cDNA sequence (Sheehy et al., Proc. Natl. Acad. Sci. USA 85:8805–8809 (1988); Cannon et al., Plant Mol. Biol. 15:39–47 (1990)). There is also evidence that 3' non-coding sequence fragments and 5' coding sequence fragments, containing as few as 41 base-pairs of a 1.87 kb cDNA, can play important roles in antisense inhibition (Ch'ng et al., Proc. Natl. Acad. Sci. USA 86:10006–10010 (1989); Cannon et al., supra). The disclosures of these articles are incorporated herein by reference.

The phenomenon of cosuppression has also been used to inhibit plant target genes in a tissue-specific manner. Cosuppression of an endogenous gene using a full-length cDNA sequence as well as a partial cDNA sequence (730 bp of a 1770 bp cDNA) are known (Napoli et al., The Plant Cell 2:279–289 (1990); van der Krol et al., The Plant Cell 2:291–299 (1990); Smith et al., Mol. Gen. Genetics 224:477–481 (1990)). The disclosures of these articles are incorporated herein by reference.

For transformation of target plants, nucleic acid fragments preferably comprising a partial or a full-length BNF5H1, BNF5H2, or BNF5H3 coding sequence, or other partial or full length CYP84 genes, are operably linked to at least one suitable regulatory sequence in the antisense orientation (for antisense constructs) or in sense orientation (for cosuppression constructs). Molecular biology techniques for preparing such chimeric genes are known in the art. The chimeric gene is introduced into a Crucifera, preferably a Brassica, plant and transgenic progeny displaying a reduced sinapine content as disclosed herein due to antisense or cosuppression are identified. Of the transgenic plants so produced, transformed plants that produce a reduced sinapine content as disclosed herein are selected for use in the invention. Experimental procedures to develop and identify down-regulated plants involve breeding techniques and sinapine content determination techniques that are known in the art. For example, sinapine may be determined by HPLC (as disclosed in the Example below). Other methods include spectrophotometric methods (as detailed in Lacki K, Duvnjak Z (1996) Comparison of three methods for the determination of sinapic acid ester content in enzymatically treated canola meals. Appl. Microbiol. Biotechnol. 45: 530–537), and the use of Near Infrared reflectance spectroscopy (as detailed by Velasco L, Matthaus B, Mollers C (1998) Nondestructive assessment of sinapic acid esters in Brassica species: I. Analysis by Near Infrared Reflectance Spectroscopy. Crop Sci. 38:1645–1650).

Since there is quite a variation in the sinapine content among the species of Brassica and other crucifers, there is no universal level of sinapine that may be tested for. Instead, an amount that represents a reduction of the natural levels in plants of interest is determined, and then plants are selected or rejected based on this amount.

As noted, it is possible to use a partial cDNA sequence for cosuppression as well as for antisense inhibition. For example, it is known that cosuppression of delta-12 desaturase and delta-15 desaturase in *Brassica napus* may be achieved by expressing, in the sense orientation, the entire or partial seed delta-12 desaturase cDNA found in pCF2-165D (see WO 94/11516, the disclosure of which is incorporated herein by reference).

Seed-specific expression of native F5H genes can also be inhibited by non-coding regions of an introduced copy of the gene (see, e.g., Brusslan, J. A. et al. (1993) Plant Cell 5:667–677; Matzke, M. A. et al., Plant Molecular Biology 16:821–830, the disclosures of which are incorporated herein by reference). A person skilled in the art may readily isolate genomic DNA containing sequences that flank F5H coding sequences and use the non-coding regions for antisense or cosuppression inhibition. The use of such non-coding regions of F5H genes is included within the scope of the present invention.

The preferred embodiment of reducing sinapine content in the seeds and ultimately seed meal of *Brassica napus* can be extended to other plants of the Crucifera family, e.g. Brassica species (*Brassica rapa, Brassica juncea, Brassica oleracea, Brassica nigra*) using the nucleotides as shown in this invention or by using F5H genes isolated from the corresponding species or from other plants. As support for this concept, it is to be noted that, lignin in transgenic tobacco was altered by antisense techniques using an alfalfa (*Medicago sativa*) caffeic acid 3-O-methyltransferase (COMT; Ni et al., 1994) or an aspen (*Populus tremuloides*) COMT (Dwivedi et al., 1994), thus providing examples for genetic alteration with genes from different species. Further, modification of lignin in transgenic tobacco plants containing a bean phenylalanine ammonia lyase cDNA was achieved due to co-suppression (Elkind et al., 1990). Thus, the possibility of altering sinapine content in transgenic Brassica using a heterologous F5H gene from a variety of sources is possible, although the use of BNF5H genes is preferred.

Also, the following examples provide similar alteration in several target species when a given enzyme production is perturbed. Cinnamyl alcohol dehydrogenase (CAD) down-regulated in poplar (Baucher et al., 1996), tobacco (Halpin et al., 1994) and pine (Mackay et al., 1997) show similar changes in the lignin composition and wood coloration. Comparable changes in lignin composition is also noted in 4-coumarate CoA ligase (4CL) down-regulated tobacco (Kajita et al., 1997) and arabidopsis (Lee et al., 1997) and COMT down-regulated aspen (Tsai et al., 1998) and maize (Vignols et al., 1995). The above examples suggest that, in different crucifers, reduction of endogenous F5H could reduce sinapine content in the seeds.

In Arabidopsis, there are three 4CL genes (At4CL1, At4CL2 and At4CL3). At4CL1 and At4CL2 are only 80% identical in their coding region, while At4CL1 and At4CL2 have only 60% identity to the coding region of At4CL3. However, all three genes were able to catalyze the conversion of similar substrates (Ehlting et al., 1999).

In the present invention, the coding sequences used for down-regulation are operably linked with regulatory sequences in a genetic construct or vector used for the transformation of a plant cell. Regulatory sequences typically do not themselves code for a gene product. Instead, regulatory sequences affect the expression level of the mutant coding sequence. Examples of regulatory sequences are known in the art and include, without limitation, promoters of genes expressed during embryogenesis, e.g., a napin promoter, a phaseolin promoter, an oleosin promoter and a cruciferin promoter. Native regulatory sequences, including the native promoters of F5H genes can be readily isolated by those skilled in the art and used in constructs of the invention. Other examples of suitable regulatory sequences include enhancers or enhancer-like elements, introns and 3' non-coding regions such as poly A sequences. All such regulatory sequences may be included in the genetic constructs employed in the present invention in ways that will be apparent to persons skilled in the art.

Techniques for the formation of sense or antisense gene constructs are well known to persons skilled in the art. This generally involves creating an expression vector by introducing the coding sequence (in reverse orientation for antisense constructs) into a plasmid having a strong constitutive or tissue specific promoter (for a general overview, see Chapters 2 and 3 of "Plant Genetic Transformation and Gene Expression, A Laboratory Manual", ed. by Draper, J. et al., pub. by Blackwell Scientific Publications (1988); see also Potrykus, et al., "Direct Gene Transfer: State of the Art and Future Potential", Plant Mol. Biol. Rep. 3: 117–128 (1985)). The disclosures of these publications are incorporated herein by reference.

The vectors thus produced may be introduced into cells of plants to be modified, again by techniques that are well known in the art (see, for example, the discussion in Watson et al. (1992) Recombinant DNA, $2^{nd}$ edition, Scientific American Books, New York, Chapters 5 and 7, etc., the disclosure of which is incorporated herein by reference). The most common techniques include Agrobacterium mediated transformation, particle bombardment, electroporation, micro- and macroinjection, pollen mediated transformation, ultra sound, silicon carbide fiber, laser induced DNA uptake, etc. (e.g. as disclosed in Keith Lindsey (1998) Transgenic Plant Research. Harwood Academic Publishers, Australia. pp: 1–55.) The methods which have been developed have allowed the stable transformation of a wide variety of organisms with exogenous DNA.

In the tests described below, in the 35S-antisense BNF5H plants, there was noticeable reduction in the BNF5H polypeptide level and a reduction of the sinapine content by up to 40%. In contrast, the BNF5H transcript level was not affected in the transgenics, except in one line. This suggests that the antisense BNF5H transcripts did not affect the transcription of the endogenous BNF5H gene or the stability of the transcript. Rather, the translation of BNF5H protein was affected. Antisense suppression results generally in a concurrent reduction of both the transcript and the polypeptide (Bourque, 1995). However, there is at least one report where the transgenic plants suffered a substantial reduction in the amount of polypeptide without encountering a similar effect on transcription (Temple et al., 1993). The mechanism of antisense suppression is not completely elucidated; antisense transcripts may hybridize with the endogenous sense transcript, destabilize the formation of the ribosomal complex and thus prevent translation (Mol et al., 1994).

The generalized pathway for phenylpropanoid metabolism depicts F5H catalyzing the formation of 5-hydoxyferulate, a precursor of sinapate, and sinapate in turn as the precursor for sinapine and for sinapoyl CoA in two bifurcated pathways (Chapple et al., 1992; Meyer et al., 1996, 1998; Ruegger et al., 1999; see FIG. 1 in Campbell and Sederoff, 1996). Sinapoyl CoA has been considered as the precursor for sinapyl alcohol, which is then polymerized into syringyl (S) lignin. This inference has, however, been modified very recently (Chen et al., 1999; Humphreys et al., 1999; Osakabe et al., 1999). Osakabe et al. (1999) demonstrated that the sweetgum CYP84 product carries out the hydroxylation of coniferyl aldehyde (ConAld) to 5-OH ConAld approximately 140 times more efficiently than that of ferulate to 5-OH ferulate, thus prompting the use of the name ConAld hydroxylase to refer to the enzyme. Further, ConAld non-competitively inhibits ferulate hydroxylation. Humphreys et al. (1999) have simultaneously shown that ConAld ($K_M$ 1 $\mu$M) but not ferulate ($K_M$ of 1 mM) is the preferred substrate for the Arabidopsis F5H, which is 75% identical in its primary structure to the sweetgum ConAld hydroxylase above. If these observations are correct, the inventors have questioned the basis for their observation that antisense suppression or cosuppression of the CYP84 members in B. napus and other crucifers diminished sinapine synthesis in the seeds, and without wishing to limit the generality of the present invention, speculate as follows. Sinapine is accumulated mostly in the cotyledons in B. napus (Fenwick, 1979). If the enzymatic properties of B. napus F5H are similar to that of the sweetgum ConAld hydroxylase, a supposed absence of ConAld in the non-lignified cotyledons would explain the participation of the B. napus enzyme in ferulate hydroxylation in vivo. Alternatively, as Humphreys et al. (1999) have speculated for Arabidopsis, an aldehyde oxidase might yield sinapate from 5-OH ConAld-derived sinapoyl aldehyde, and thus any constraint on the flux to 5-OH ConAld would also diminish sinapine synthesis.

As Lindberg and Negishi (1989) have shown, a single aa substitution in the coumarin 7 hydroxylase, a P450 monooxygenase, can expand its substrate specificity to include a steroid. Interestingly, the Arabidopsis F5H but not the sweetgum gene product (both from a yeast expression system) can hydroxylate coniferyl alcohol (Humphreys et al., 1999; Osakabe et al., 1999), suggesting potential differences in the catalytic repertoire of CYP84 enzymes as well. The apparent minor differences among the BNF5H gene products in Brassica may have some enzymological implications.

Utility Implications of BNF5H Downregulation

Seed meal (especially canola meal) is a significant source of protein supplement in animal feed. The inventors' results show that it is possible to achieve a substantial measure of reduction in the sinapine content by down-regulating F5H genes, e.g. BNF5H, thus offering an avenue for improving the meal quality. Besides sinapine reduction, this approach may offer other collateral benefits. Cherney et al. (1991) had found that the midrib mutants of maize and sorghum, which are lower in the relative content of S lignins, are more digestible. The digestibility of forage is inversely related to its lignin-derived methoxyl content (Dixon et al., 1996). The S lignin contains two methoxyl groups on each aromatic ring, in contrast to the guaiacyl (G) lignin that contains one. Thus, the feed would be more digestible if it contained less S lignin even if the total lignin content of a feed material, typically G+S lignins, remained unaltered. The F5H null mutant of Arabidopsis has very little S lignin; interestingly, CaMV promoter-directed production of F5H in this mutant restores the S lignin content, and the use of a cinnamate 4-hydroxylase promoter instead renders the lignin almost completely S-type (Meyer et al., 1998; Marita et al., 1999).

Thus, the down-regulation of the F5H genes in *B. napus* and other crucifers may have a favorable impact on the lignin composition and meal digestibility.

Commercial Production of Seed Meal

Transgenic seed produced according to the present invention may be converted to seed meal by techniques known in the art, which are generally intended primarily for removal of the oil content of the seed, but also produce seed meal as a by-product. In a typical process described by way of example, the seed typically is tempered by spraying the seed with water to raise the moisture to, for example, 8.5%. The tempered seed is flaked using smooth rollers with, for example, a gap setting of 0.23 to 0.27 mm. Heat may be applied to the flakes to deactivate enzymes, facilitate further cell rupturing, coalesce the oil droplets and agglomerate protein particles in order to ease the extraction process.

Typically, oil is removed from the heated seed flakes by a screw press to press out a major fraction of the oil from the flakes. The resulting press cake contains some residual oil.

Crude oil produced from the pressing operation typically is passed through a settling tank with a slotted wire drainage top to remove the solids expressed out with the oil in the screw pressing operation. The clarified oil can be passed through a plate and frame filter to remove the remaining fine solid particles.

Seed press cake produced from the screw pressing operation can be extracted with commercial n-Hexane. The seed oil recovered from the extraction process is combined with the clarified oil from the screw pressing operation, resulting in a blended crude oil.

The resulting extracted press cake is the commercial product of interest in the present invention, that may then be used for animal feed and supplements. The reduced sinapine content of the seeds produced according to the present invention could make the resulting seed meal more commercially valuable and useful as it is more palatable to animals and possibly more digestible.

It is also to be noted, however, that seed meal according to the present invention may be produced directly, i.e. without oil extraction, simply by collecting a mass of the seeds and, if necessary, crushing, flaking, rolling, compressing or otherwise rendering them less viable for growth and more digestible in animals.

Incidentally, it should be noted that, in the experimental methods of the present invention, the sinapine content of plant seeds is determined. While it is the sinapine content of seed meal that is of interest, it is well known that sinapine remains in the seed meal following the removal of seed oil, so the sinapine content of seeds prior to oil removal represents the content of sinapine in seed meal after oil extraction.

Having described the invention in general terms above, the following disclosure provides experimental data in support thereof.

EXAMPLE

Materials and Methods

Plant Material and Growth Conditions

*Brassica napus* cv Westar, *B. oleracea* cv Horizon and *B. rapa* cv Green Valiant plants were used in this study. The plants were planted in Rediearth® (Grace Horticultural Products, Ajax, ON, Canada) potting medium, watered with a fertilizer solution (0.2g/L NPK 20:20:20; Plant Products Company, Brampton, ON, Canada) and grown in a chamber under 16 hour light/25° C. and 8 hour dark/ 20° C. cycle. The light intensity was 380 µmol m$^{-2}$ S-1 PPFD. The samples were collected, frozen in liquid nitrogen and stored at −80° C. until needed.

Chemicals

Purified sinapate esters used as the reference standards were initially the kind gifts of Drs. D. I. McGregor (Agriculture and Agri-Food, Saskatoon, Canada) and B. E. Ellis and S. X. Wang (Univ. of British Columbia, Canada), and subsequently were isolated and purified from *B. napus* by Ms K. Gossen (National Research Council-Plant Biotech Institute, Canada). HPLC grade solvents were purchased from J. T. Baker (Phillisburg, N.J., USA), and all other reagents were of reagent grade from Sigma Chemical Company (St. Louis, Mo., USA).

DNA and RNA Methods

The nucleic acid related enzymes used were from Life Technologies, Ontario, Canada. Oligonucleotide synthesis and DNA nucleotide (nt) sequencing were conducted at the National Research Council, DNA Technologies Unit, Canada. A *B. napus* stem cDNA library in Uni-ZAP XR® vector (Stratagene) constructed in the inventors' laboratory according to the supplier's instruction manual was screened with an Arabidopsis F5H cDNA probe (Meyer et al., 1996; kind gift of Dr. C. C. Chapple) to isolate the *B. napus* F5H cDNA clones. The plasmids from the phages were isolated according to the supplier's instruction manual. The clones with insertions >1.5 kb were selected for determining the nt sequence in both directions. Lasergene Biocomputing Software® (DNASTAR Inc., Madison, Wis.) was used for sequence analysis.

Genomic DNA was isolated from leaves using a Nucleon PHYTOPURE® plant DNA extraction Kit (Amersham, Buckinghamshire, England). An amount of 15 µg of genomic DNA digested with restriction endonucleases was separated by 1% TAE agarose gel electrophoresis (Sambrook et al., 1989) and transferred on to a GeneScreen Plus® membrane (NEN Life Science Products, Boston, Mass. USA). The membrane was prehybridized at 42° C. for 3 hours in 10 ml of Prehybridization Buffer (Sambrook et al., 1989; 50% formamide, 5× Denhardt's reagent, 5×SSC, 0.1% SDS, 100 µg mL-1 denatured salmon sperm DNA). A [32P]dCTP-labeled F5H probe was synthesized from a fragment of BNF5H1 cDNA (nt 256 to 702) using a Rediprime II® random primer labeling kit (Amersham). Hybridization with the probe was done overnight in 10 ml of hybridization buffer (Prehybridization Buffer plus 2% w/v dextran sulphate). After hybridization, the membrane was rinsed twice with a solution of 0.2×SSC, 0.1% SDS (Sambrook et al., 1989); washed twice with 0.2×SSC, 0.1% SDS for 15 min at 50° C. and once with 0.1×SSC, 0.1% SDS for 30 min at 65° C. It was then exposed to an X-ray film (Fuji) for 1–5 days with Quanta III intensifying screens (DuPont).

Total RNA from various tissues was isolated using TRIzol reagent (Life Technologies) according to the supplier's protocol. Northern blot analysis was done with 15 µg of total RNA that was electrophoretically separated and transferred to a GeneScreen Plus® membrane (Sambrook et al., 1989). The BNF5H probe was prepared as above.

PCR Analysis

The introns in the genomic segments were amplified with the following primer pairs:

Pair 1, for BNF5H1 and BNF5H2:
  5'-CGAGTCATGGGCTTCTGTT-3' [SEQ ID NO:7] and
  5'-TATCGCTGACGCTACCGTTCC-3' [SEQ ID NO:8];

Pair 2, for BNF5H3:
  5'-AGATGAGGAAAGTGTGT-3' [SEQ ID NO:9] and
  5'-CCGTAATAACTCCGTTAAG-3' [SEQ ID NO:10].

The first primer in each of these pairs and in the primer sets outlined below is based on the sense strand, and the second primer is derived from the non-coding strand of the cDNA clone sequences deposited in GenBank (See Results below). PCR was set up in a 50-µl volume that contained 250 ng of genomic DNA as template, 1×PCR buffer (Life Technologies), 1.5 mM MgCl2, 200 µM of each dNTP and 50 pmol of each gene specific primer. The samples were heated at 94° C. for 3 min to denature the template, then cooled to 72° C., and immediately 2.5 U of Taq DNA polymerase were added. The amplification was conducted for 30 cycles in a Perkin-Elmer® DNA Thermal Cycler at a setting of 94° C. for 45 sec, 56° C. for 1 min and 72° C. for 2 min for each cycle extension step at 72° C. for 10 min. The positive controls contained as the template 20 ng of BNF5H 1, -2 or -3 cDNA clones and the negative control contained only the primers in question.

Poly A+mRNA was isolated from 5 mg of total RNA from various tissues using Oligotex® mRNA midi kit (Qiagen, Mississauga, Ontario, Canada). Two µg of the eluted mRNA sample was used for the first strand cDNA synthesis by Superscript Rnase H-Reverse Trascriptase (Life Technologies) following the manufacturer's protocol. The single-stranded cDNA was dissolved in 100 µl of TE buffer and the PCR was set up with 2.5 µl of cDNA template as described above and amplification was conducted for 25 cycles.

RT-PCR with total RNA isolated from various tissues was done as follows. First strand cDNA was synthesized from 10 µg of total RNA by Superscript RNase H-Reverse Transcriptase (Life Technologies). The reaction was stopped by incubating at 68° C. for min, and the total volume made up to 50 µl with de-ionized water. PCR was set up in a 50 µl reaction volume containing 1 µl of the above cDNA preparation as the template, 1× PCR buffer (Life Technologies), 1.4 mM MgCl2, 200 µM of each dNTP, 50 pmol of each of the two gene specific primers for BNF5H1, -2, or -3 and 2.5 U of Platinum Taq DNA polymerase (Life Technologies). After an initial denaturation of DNA for 2 minutes, amplification was conducted for 15 cycles as described above except that the annealing temperature was at 61° C. for 1 min. The positive controls contained 20 pg of relevant BNF5H cDNA as the template, and the negative control contained the primers but no template. After agarose gel electrophoresis, Southern blot hybridization was done with a probe derived from BNF5H2 (nt 1310–1695) that hybridizes to all three BNF5H amplification products.

Specific primer sets for each of the three BNF5H genes was used: Set A and B for BNF5H1, and Set C and D for BNF5H2, and Set E and F for BNF5H3. The nt sequence of these sets are as following:

Set A
  5'-TTCTCGAACCGACCAGCT-3' [SEQ ID NO:11] and
  5'-ACAAATAAGGCGCGTGCT-3' [SEQ ID NO:12]
Set B
  5'-GAGTGGGCATTGACTGAATTAC-3' [SEQ ID NO:13] and
  5'-CCATACCAACCACCTTTCC-3' [SEQ ID NO:14]
Set C
  5'-GGGCATTGACTGAGTTAT-3' [SEQ ID NO:15] and
  5'-CCACAGCTCAAGAACCATC-3' [SEQ ID NO:16];
Set D
  5'-CGCGACAAGAACTCTTGGGTTGAT-3' [SEQ ID NO:17] and
  5'-CCACGTTCAAGAACCATCAACC-3' [SEQ ID NO:18];
Set E
  5'-ACCCTAAATCTTGGCCTGACG-3' [SEQ ID NO:19] and
  5'-CCATACCTACTACCAACCCTTCG-3' [SEQ ID NO:20];
Set F
  5'-TTAGAACCGGGAGTAGC-3' [SEQ ID NO:21] and
  5'-CCTATTACCAACCCTTCG-3' [SEQ ID NO:22].

Genetic Transformation of Plants

The plasmids (designated pJOY) for *Agrobacterium tumefaciens*-mediated transformation were constructed by inserting a 1.8-kb EcoR I fragment of the BNF5H1 cDNA (this fragment lacks the polyA region) in the sense or anti-sense orientation (FIG. 14). All of the plasmids are based on the binary vector pHS723 constructed in the inventors' laboratory (Hirji et al., 1996). *A. tumefaciens* GV3101 [pMP90] (Koncz and Schell, 1986) derivatives with the pJOY plasmids were obtained by the freeze-thaw method described by An et al. (1988). Genetic transformation of *B. napus* hypocotyl explants and regeneration of plants were according to Moloney et al. (1989). Putative transgenics were selected by kanamycin resistance and confirmed as transgenics by X-Gluc-based GUS assay (Jefferson et al., 1986) afforded by the bi-functional selection marker (GUS::NPTII; Datla et al., 1991) within the T-DNA (FIG. 14). The primary lines with a single-copy of the transgene were identified following Southern blot of Hind III-restricted DNA and probing with a GUS gene fragment. These were selfed to obtain $T_0$ seeds. Ten $T_1$ plants were selfed to obtain $T_2$ seeds. Seedlings from $T_2$ seeds were screened by the GUS assay to identify homozygous $T_2$ seed lots. Isolation of F5H protein and production of antisera A partial F5H cDNA lacking the N-terminal 170 amino acids was ligated in frame into a pRSET protein expression vector (Invitrogen) containing N-terminal Histidine tags. The resultant plasmid (pRAM5) was transformed into BL21DE3 *E. coli* strain. As a control, pRSET vector alone transformed BL21DE3 *E. coli* strain was used. An overnight culture of the BL21DE3 *E. coli* carrying the recombinant plasmid grown at 30° C. was inoculated at 1:25 into fresh 50-ml LB medium. The bacterial culture was then treated with 1 mM IPTG at OD=0.7 at 600 nm and incubated for another 3 hours. Bacterial cells were harvested, lysed in 6M guanidine-HCL and the protein purified using Ni-NTA columns (Qiagen) using varying levels (20–200 mM) of imidazole concentration. Protein fractions were analyzed on 10% SDS-PAGE. The protein band that correspond to expected F5H was cut and used for raising antisera in rabbits according to the standard protocols (Harlow and Lane, 1988).

Immunoblot Analysis 1 g of *B. napus* stem was ground in liquid nitrogen and extracted in 1.5 ml of buffer [50 mM Hepes pH7.5, 1 mM EDTA pH7.5, 10% glycerol]. The extract was centrifuged at 6000 g for 30 min at 4° C., and the supernatant was assayed for protein concentration by the modified Bradford method (Bio-Rad, Hercules, Calif.). An amount of 15 µg protein-equivalent of the extract in the gel loading solution [50 mM Tris pH 6.8, 2.3% SDS, 5% β-mercaptoethanol, 10% glycerol] was boiled for 10 min and separated in 10% SDS-PAGE in duplicate gels. The polypeptides were electroblotted onto a PVDF membrane (Hybond-P; Amersham), and the membrane was probed with the BNF5H antisera, followed by horseradish peroxidase-conjugated donkey anti-rabbit IgG (Amersham), and chemiluminescent detection with a ECL+Plus western blotting system (Amersham) according to the supplier's instructions. The duplicate membrane and also immunoprobed membrane after chemiluminescent detection were stained with 0.1% amido black in a 45% methanol-5% acetic acid solution to verify equal loading and transfer of protein.

HPLC Analysis of Phenolics

Ten seeds, including the seed coat, or 10 mg of freeze dried leaves from 21 day old seedlings were ground in 500 µl of 80% methanol, incubated at 4° C. for 1 h and frozen at −80° C. for 1h. The extract was thawed and centrifuged at 20000 g for 15 min to obtain the supernatant. The pellet was re-extracted with 500 µl of 80% methanol at 4° C. for 1 h, and centrifuged as above. The two supernatants were pooled, and 20 µl of the pooled extract was run on a Nucleosil® C18 AB HPLC column (Alltech, Deerfield, Ill.) using an acetonitrile/phosphoric acid (1.5%) gradient of 10 to 30% over a 35 min period in a Varian Vista 5500 HPLC instrument. UV absorbance at 330 nm was detected with a Varian Model 9065 Polychrom. The average of sinapine and sinapoyl malate (SM) contents per mg of vector alone transformed transgenic seeds or leaves (vector control—VC) was calculated as 100%. All other data was calculated as percentage sinapine or SM content of vector control plants. The standard error was calculated from three replications for each transgenic plant.

Results

Isolation of Three Unique F5H cDNA Clones from *B. napus*

Five cDNA clones (BNF5H) hybridizing to an Arabidopsis F5H probe were isolated from a stem cDNA library of *B. napus*. The cDNA inserts in two clones appeared truncated but otherwise identical in sequence to the insert in another clone (BNF5H1). Thus, only BNF5H1 and the remaining two clones, BNF5H2 and BNF5H3 were characterized further. These three showed nt sequence polymorphism in the open reading frame (ORF) and a significant difference in the 3'-untranslated (UTR) sequences. The nt sequences of the inserts in these clones have been deposited in GenBank Accession numbers AF214007, AF214008, AF214009).

The insert in BNF5H1 (1880 bp) has a 38-nt 5'-UTR, a 1560-nt ORF, and a 282-nt 3'-UTR while BNF5H2 (1884 bp) has a 51-nt 5'-UTR, a 1560-nt ORF and a 273-nt 3'-UTR. The first ATG in the putative ORF of BNF5H2 is preceded by an in-frame TAG sequence at position −36 relative to the ATG. The flanking sequences in both BNF5H1 and BNF5H2 (AAT ATG GAG) have the consensus nt present in the plant translational initiation context sequence (Joshi et al., 1997). Thus, the ORF of 1560 nt present in BNF5H1 and BNF5H2 is predicted to encode a 520-aa polypeptide with a molecular weight of 58.5 kD. The third cDNA clone (BNF5H3) with an insert of 1835-nt appeared to be truncated at the 5'-region up to the 18$^{th}$ nt of the ORF. This clone has a 292-nt 3'-UTR. The sequences are shown in FIGS. 3, 4 and 5.

The ORFs in BNF5H1 and 2 are very similar to each other (98% nt sequence identity; 99% aa sequence identity). They are similar to the *A. thaliana* F5H ORF (520 aa; Meyer et al., 1996) at the nt (90% identity) and aa (93% identity) levels. The near-complete ORF in BNF5H3 (514 aa) also shows the same level of identity to the corresponding portion but lacked a codon for Pro at position 39 which is present in the other F5Hs. The Arabidopsis F5H is the first member of CYP84, a new family of cytochrome P450-dependent monooxygenases (Meyer et al., 1996). Recently, a coniferaldehyde 5-hydroxylase clone from *Liquidambar styraciflua* has been isolated (Osakabe et al., 1999). This CYP84 member is 72% identical to Arabidopsis and BNF5H protein. The *B. napus* F5Hs also contain a high degree of amino acid sequence conservation in the proline rich region immediately following the N-terminal hydrophobic region and in the C-terminal heme binding region (residues P450 FGXGRRXCXG460 of BNF5H1) which is characteristic to P450 monooxygenases. Thus, the three BNF5Hs were deemed to belong to CYP84. Further, as alluded to above, the three cDNA clones were considered to represent three CYP84 genes. Additional evidence for this is provided below.

*B. napus* and its Progenitors have at Least Two Groups of F5H Genes

The molecular relationship of BNF5H1, -2 and -3 was studied further by examining the 3'-UTR and the ORFs in the three cDNA clones, and the introns in the corresponding genomic segments. The nt sequence of the 3'-UTR of BNF5H1 differs from that of BNF5H2 by 13% and from that of BNF5H3 by 37%. Similarly, the 3'-UTR of BNF5H2 differs from that of BNF5H3 by 37%. Aside the absence of a Pro codon in BNF5H3, the ORFs of the three clones showed nt polymorphism as originally detected by restriction digestion patterns (data not shown) and subsequently by nt sequence analysis.

A genomic clone was identified by probing a *B. napus* cv. Westar library with a BNF5H1 probe. A preliminary analysis showed that the region corresponding to the central one-third of the ORF contained two introns (data not shown). Two sets of PCR primers (see Methods) were used as individual pairs to amplify this region from a *B. napus* genomic DNA sample, and the independently derived amplicons (0.95 kb or 1.1 kb) were cloned into pBluescript® SK+ (Stratagene). The inserts in nine of these were sequenced completely. Both the 0.95-kb and 1.1-kb category contained two introns, and the exon regions. The exon sequence allowed assignment of the amplicons to the three cDNA clones. Collectively, three types of amplicons corresponding to BNF5H1, -2 and -3 were found. The congeneric introns thus identified were compared among themselves. The two introns are situated at identical positions in all three genes with respect to the stop codon (FIG. 9). However, the length and nt sequence show significant differences. The introns of BNF5H1 and -2 are more similar to each other than to those of BNF5H3. Further, the nt sequence dissimilarity scores for the introns shown in FIG. 9 support the relationship gleaned from the comparison of the UTRs. Thus, these results collectively establish two organizational groups of BNF5H genes within the *B. napus* CYP84 family, one comprising BNF5H1 and -2 and the other BNF5H3.

The cultivated *B. napus* used here is a descendent of a natural amphidiploid (n=19) containing the genomes of both *B. rapa* (n=10) and *B. oleracea* (n=9). It was of interest to find the association, if any, of the above gene groups to the diploid species. Southern blot analysis of genomic DNA detected four bands in *B. napus* and two in each of the two cultivated species of *B. rapa* and in *B. oleracea* (FIG. 10), suggesting the presence of at least four genes in *B. napus* and at least two in the other species. The third band in the Hind III digest of *B. oleracea* might be due to an additional gene or due to an internal cleavage site in one of the genes. The attribution of the individual genes to the *B. rapa* or *B. oleracea* lineage was done by amplification of the genomic DNA with gene-specific primers from the coding region. The specificity of these primer pairs was ascertained with the respective cDNA controls. As shown in FIG. 11, BNF5H3 is present in both *B. rapa* and *B. oleracea*, BNF5H1 only in *B. rapa* and BNF5H2 only in *B. oleracea*.

As expected, *B. napus* yielded the amplicons for all three genes. The above-noted molecular relationship among the three BNF5H genes vis-à-vis the genealogical relationship was confirmed from the conservation of similarity among the amplicons at their nt sequence level. For example, the BNF5H1 amplicon was more similar to its counterpart from the other two species than to the amplicons of BNF5H2 or BNF5H3 from any of the three species (data not shown). This is noteworthy in view of the closer relationship of BNF5H1 to BNF5H2 than to BNF5H3.

Expression Profile of the BNF5H Genes in *B. napus*

Figure 12:
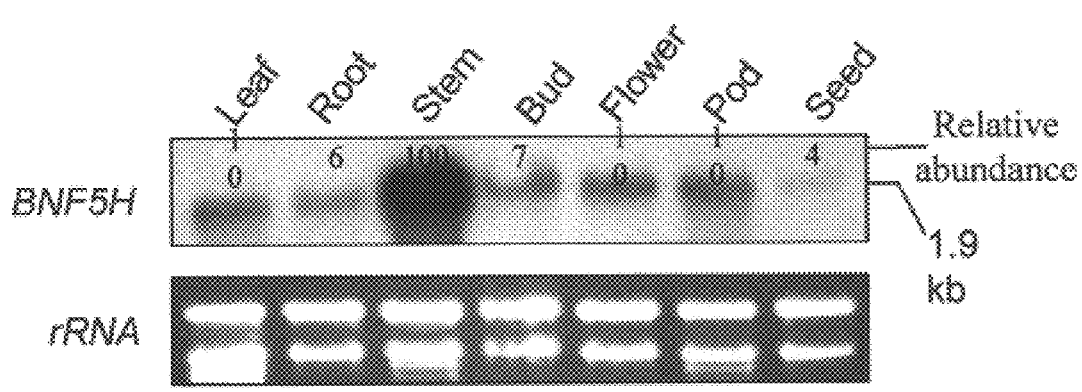
FIG. 12 shows a Northern blot analysis of BNF5H gene expression in Brassica napus tissue. Twenty μg of total RNA for each sample was electrophoresed, blotted and probed with a BNF5H1 (nt 256–702) cDNA probe. rRNA, Ethidium bromide-stained ribosomal RNA. The relative abundance of BNF5H transcript was measured in a Molecular Dynamics PhosphorImager.
Figure 13:
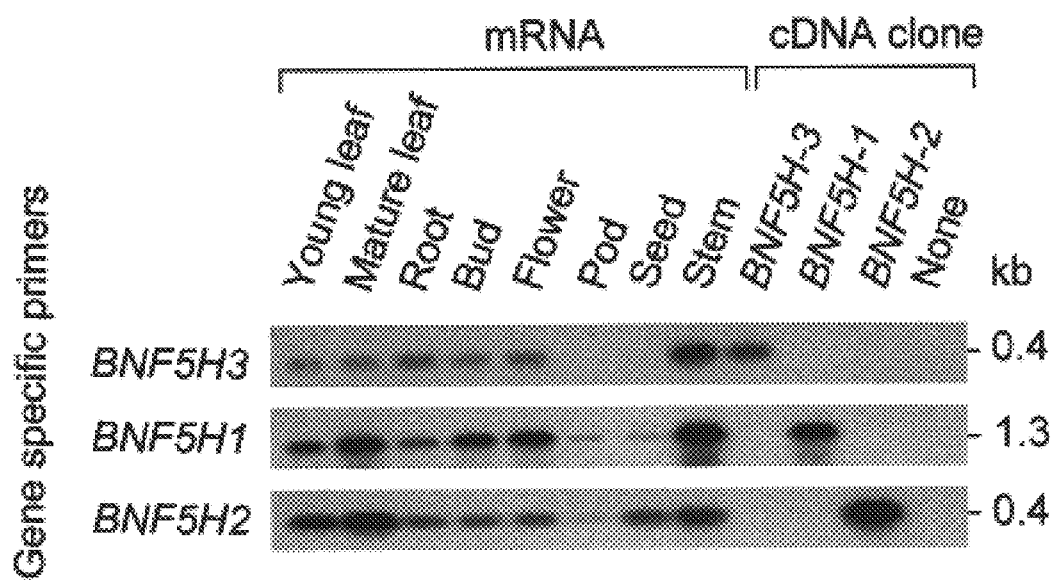
FIG. 13 shows an RT-PCR analysis of 10 μg Total RNA with gene-specific primers. The controls with the BNF5H cDNAs or no template DNA are as shown. The primer sets used here (see Methods) were as follows: Set A for BNF5H1, Set D for BNF5H2 and Set E for BNF5H3. The BNF5H1-specific primers used here did not yield an intron-containing amplicon indicating absence of genomic DNA contamination in the template.

Northern blot analysis of total RNA from various parts of *B. napus* with an BNF5H cDNA probe showed a very abundant transcript of 1.9 kb in the stem, and much less in the root, leaf, pod, bud and the least in the seed tissue (FIG. 12). The expression of other phenylpropanoid pathway genes, phenylalanine ammonia-lyase and cinnamate 4-hydroxylase also followed this general pattern, but the cinnamate 4-hydroxylase gene expression was almost equally abundant in both stem and root tissue (data not shown). A 25-cycle RT-PCR of polyA+RNA with gene specific primers showed an amplicon of predicted size for each primer pair in all these tissues, indicating expression of the three genes in these tissues (data not shown). The RT-PCR analysis was repeated with total RNA and with fewer cycles (15-cycle reaction) to provide a better distinction of the relative transcript abundance. A Southern blot hybridization analysis of the resulting amplicons was done with a common probe as described in Methods (FIG. 13). In general, the stem tissue showed an abundant expression of all three genes, and the pods and seeds showed the least transcript abundance for all three genes. BNF5H3 was expressed nearly uniformly in young and old leaf, root, bud, and flower but much less in pods and seeds. Interestingly, BNF5H2 expression was greater in the seed tissue than in the root, bud, flower or pod tissue. Also, it showed a high level of expression in mature leaves. BNF5H1 also showed a variation in the expression levels. Thus, while all the tissues that were examined here expressed all three genes, there were differences in the level of expression. This experiment was repeated with different primer pairs that confirmed the expression profile.

Figure 15:
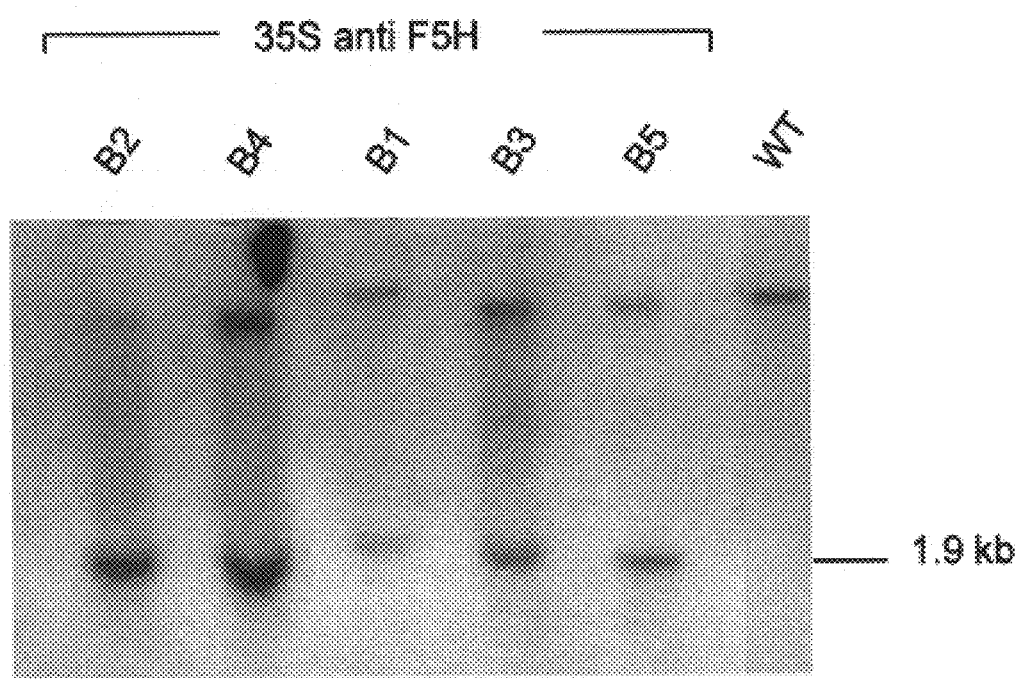
FIG. 15 is a Southern blot analysis of homozygous transgenic plants of *Brassica napus* originally transformed by 35S antisense F5H construct (pJOY42). Hind III digested genomic DNA from transgenic plants was probed with a F5H cDNA probe (bases 1452 to 1718 of BNF5H1). The 1.9 kb DNA fragment present in the transgenic plants corresponds to a Hind III fragment of the T-DNA as shown in FIG. 14.
Figure 17:
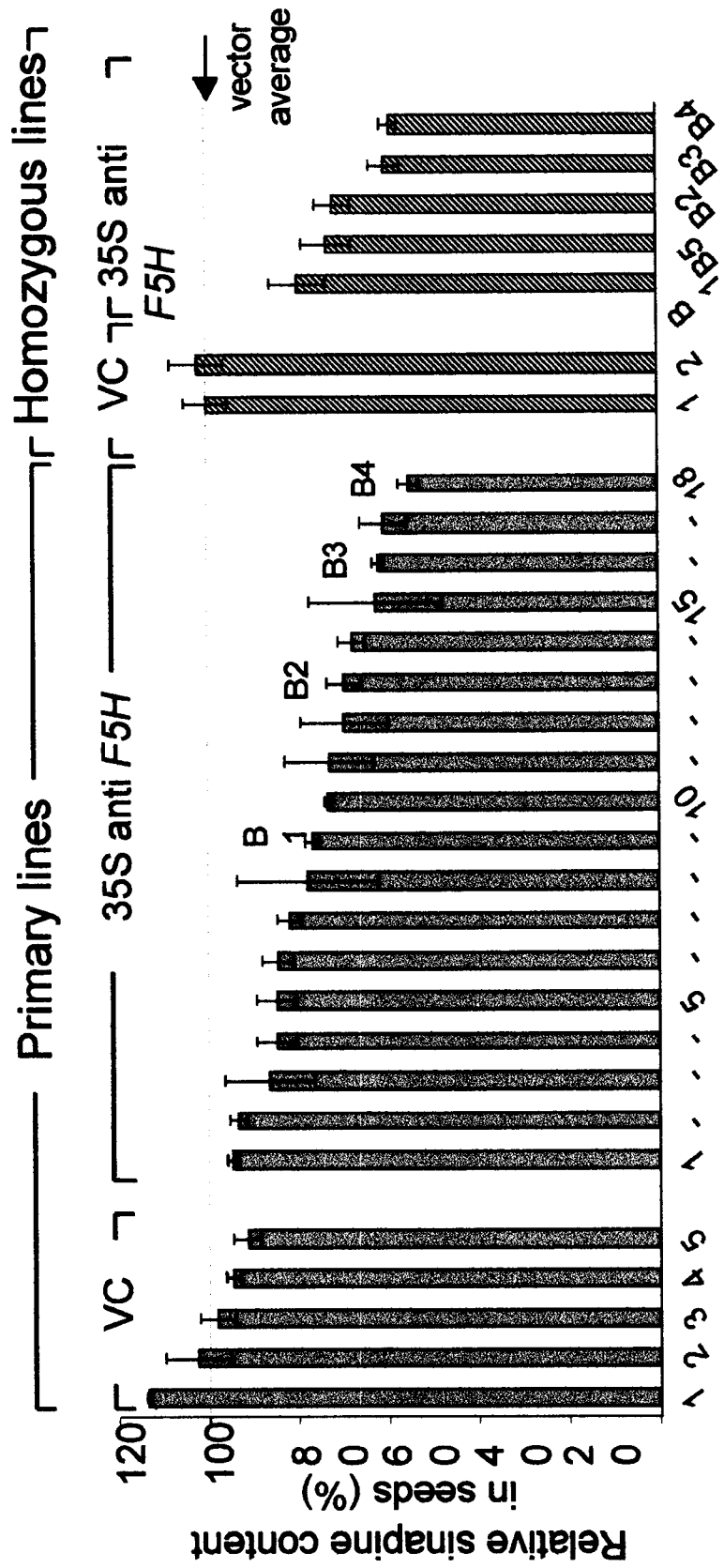
FIG. 17 shows a HPLC analysis of the sinapine content of the seeds from CaMV35S-antisense BNF5H1 (shown in the illustration as 35S anti F5H) transgenic lines. The alphanumeric designation in the bars of the "Primary lines lot" identify the parents of the corresponding homozygotes in the "Homozygous lines lot." There are additional homozygotes for which no corresponding primary line data were generated here because of the sample size in the parents. Three replications were done for each transgenic line. The sinapine content in mg g$^{-1}$ mature seeds for the homozygous samples were as follows: Vector control (VC); Line 1 (9.1±0.1); Line 2 (8.8±0.3); B1 (7.1±0.8); B2 (6.4±0.6); B3 (5.4±0.5); B4 (5.3±0.3), and B5 (6.5±0.8). homozygous vector control, 9.0±0.3 mg g$^{-1}$ mature seeds, was taken as 100% for the relative values shown.

F5H Transgenic Lines of *B. napus*, and Their Molecular Genetic and Biochemical Attributes The inventors of the present invention examined the impact of constitutive anti-sense suppression of BNF5H by generating transgenic lines with inverted BNF5H1 under the control of a CaMV35S promoter (PJOY 42—FIG. 14). Integration of the T-DNA region in the transgenic plants was analysed by Southern blot analysis (FIG. 15). Hind III-restricted genomic DNA of these were probed for T-DNA copy number as noted in FIG. 14 to find the lines for generating homozygotes (discussed below). From 22 transgenic lines, 18 were assayed and these showed various levels of sinapine in the $T_0$ seeds (FIG. 17; see Primary lines lot). As with the other transgenic lines above, homozygotes were derived and the seeds from five lines were assayed for their sinapine content. It was reduced in all of them, by up to 40% in two lines (FIG. 17; see Homozygous lines lot).

Figure 16:
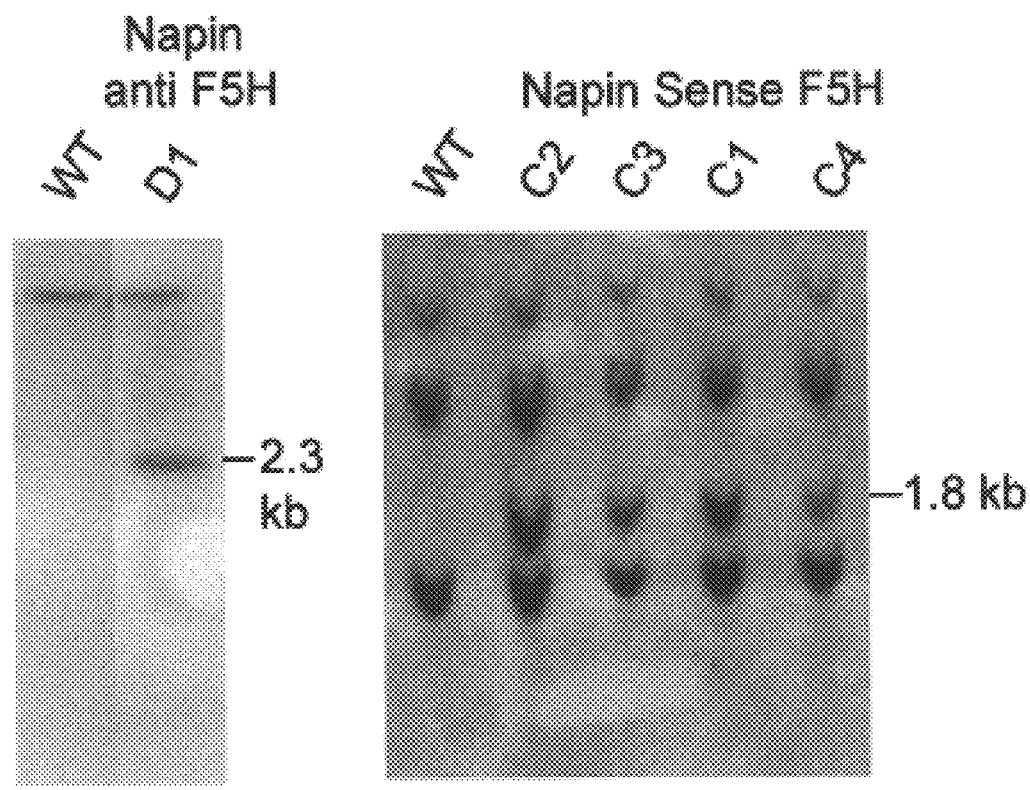
FIG. 16 is a Southern blot analysis of homozygous transgenic plants of *Brassica napus* originally transformed by Napin Sense F5H (pJOY43) and Napin antisense F5H (pJOY44). Hind III digested genomic DNA from transgenic plants was probed with a F5H cDNA probe (bases 1452 to 1718 of BNF5H1 for pJOY44 and bases 256 to 702 of BNF5H1 for pJOY43). The 1.8 and 2.3 kb DNA fragment present in Napin Sense F5H and Napin antisense F5H transgenic plants corresponds to a Hind III fragment of the T-DNA as shown in FIG. 13.
Figure 18:
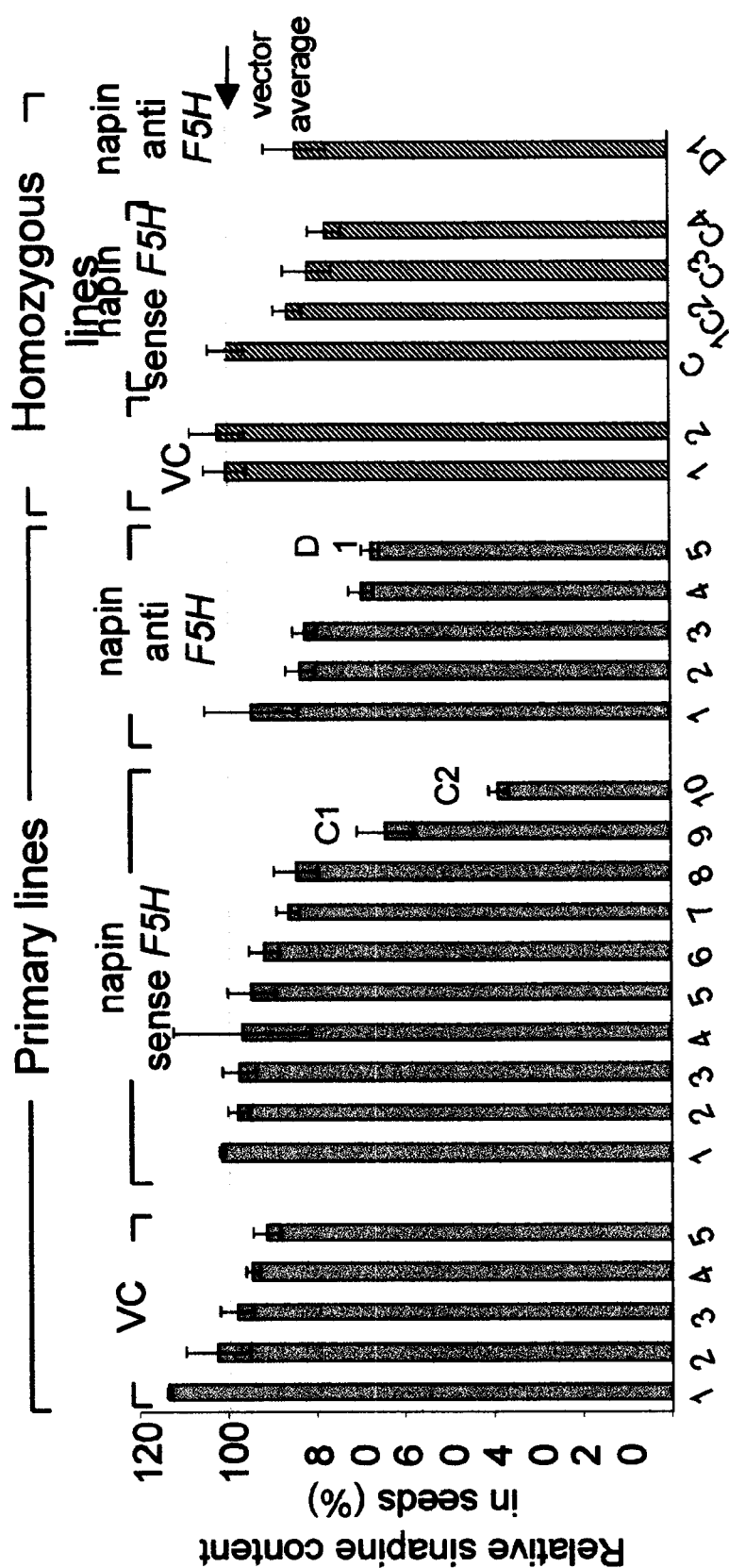
FIG. 18 shows a HPLC-analysis of the sinapine content of the seeds from transgenic lines with BNF5H1 (shown in the illustration as F5H) under the control of a napin promoter. Three replications were done for each transgenic line. The alphanumeric designation in the bars of the "Primary lines lot" identify the parents of the corresponding homozygotes in the "Homozygous lines lot." There are additional homozygotes for which no corresponding primary line data were generated here because of the sample size in the parents. The sinapine content in mg g$^{-1}$ mature seeds for the homozygous samples were as follows: Vector control (VC) Line 1 (9.1±0.1); Line 2 (8.8±0.3); C1 (8.9±0.2); C2 (7.6±0.5), C3 (7.3±0.8), C4 (6.9±0.6) and D1 (7.5±1.1). The a homozygous vector control, 9.0±0.3 mg g$^{-1}$ mature seeds, was taken as 100% for the relative values shown.

A total of 15 transgenics with pJOY43 (napin-sense BNF5H1) and 6 with pJOY44 (napin-antisense BNF5H1) were obtained. Hind III-restricted genomic DNA of these were probed for T-DNA copy number as noted in FIG. 14 to find the lines for generating homozygotes (discussed below). Integration of the T-DNA region in the transgenics was analysed by Southern blot analysis (FIG. 16). The napin promoter is seed-specific, and its activity spans the mid-phase of seed development (Joseffson et al., 1987) during which sinapine is synthesized (Vogt et al., 1993). The sinapine content of the mature seeds ($T_0$ seeds) from the primary transgenic lines was assayed on the assumption that perturbation of BNF5H gene expression would show an alteration. Not all primary lines could be assayed because of the poor seed yield in some. None of the ten napin-sense BNF5H1 transgenics showed an enhanced sinapine content, but two of them had much less sinapine than the rest or the control (FIG. 18; see Primary lines lot). Four of the five napin-antisense BNF5H1 lines also showed a reduction (FIG. 18; see Primary lines lot). The $T_0$ seeds from those primary transgenic lines with a single-T DNA insertion were retained for deriving homozygotes: $T_0$ seeds to give $T_1$ plants and the seeds from these ($T_1$ seeds) to give $T_2$ plants and $T_2$ seeds therefrom. The homozygotes were identified by their non-segregating GUS+phenotype from a screening of ≈40 seedlings from each plant. The average concentration of extractable sinapine in the two homozygotes of the pHS723 transgenic lines (vector control) was 9.0±0.3 mg g−1 seed. This value was taken as 100% for all comparisons. Surprisingly, the $T_2$ homozygous seeds from napin-sense lines also contained less sinapine (FIG. 18; the homozygous lines lot), but the reduction was not as strong as the apparent reduction in the TO samples from the tissue culture-derived plants (the primary lines lot). The single homozygous napin-antisense line also showed a modest reduction.

Figure 19:
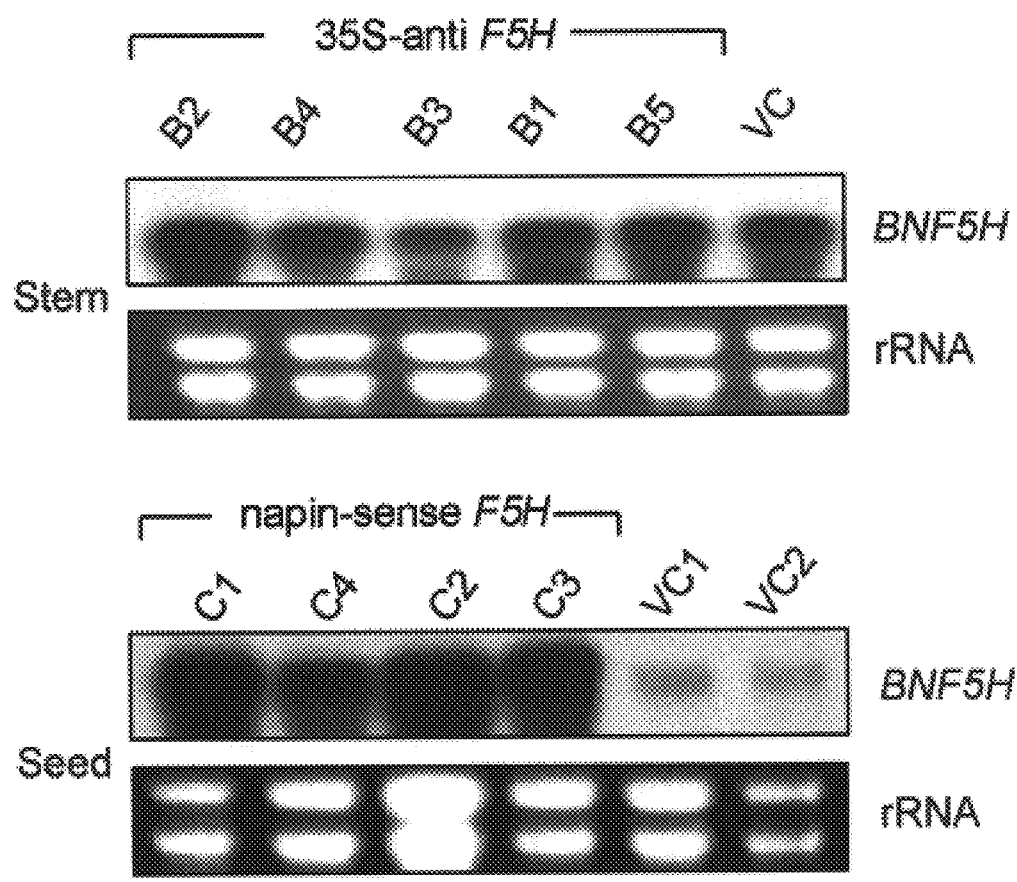
FIG. 19 shows a Northern blot analysis of homozygous (T$_2$) transgenics with a BNF5H probe. Fifteen μg of total RNA from the bottom 10 cm portion of stem tissue from each of the 35S antisense-BNF5H1 transgenics or from the seeds of each of the Napin sense-BNF5H1 transgenic lines of *Brassica napus* was electrophoresed, blotted and probed; the seeds from the latter were collected over a 20 to 30-day period after flowering in each line. VC, empty vector transgenic line control; rRNA, Ethidium bromide-stained ribosomal RNA. Here and in subsequent figures, the alphanumeric designations B1 through B5 and C1 through C4 denote homozygous transgenic lines (T$_2$), whose lineage has been referred to in FIGS. 17 and 18.
Figure 20:
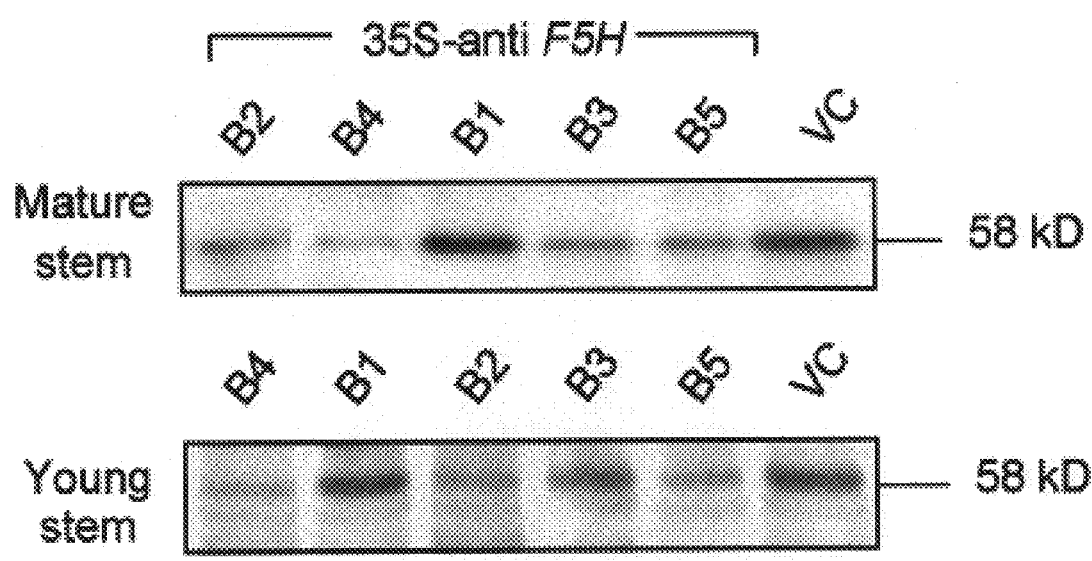
FIG. 20 shows an immunoblot analysis of 35S antisense-BNF5H1 stem extracts. Fifteen μg of total protein extracts were boiled, separated in SDS-PAGE, blotted and probed with rabbit antisera raised against a truncated recombinant BNF5H produced in *Escherichia coli*. VC, vector-alone transgenic line. Old and young stem refers to bottom 10–15 cm and upper 15 cm of stem, respectively. Equal loading of protein was verified by amido black staining of the membranes.

The BNF5H expression in the homozygotes was analyzed in northern and western blots. The older stem (bottom 10–15 cm) tissue had been found to have the most abundant expression of the native BNF5H gene (FIG. 12), and this tissue was examined in the 35S antisense-BNF5H1 transgenics (FIG. 19). With the exception of Line B3, the transgenic lines did not show any significant reduction in the BNF5H transcript level. A similar BNF5H gene expression pattern was also observed when the top 15-cm stem was probed (data not shown). Napin-sense BNF5H1 transgenic seeds showed a very abundant BNF5H transcript level as compared to the vector-alone transformed plants (FIG. 19), as expected for the expression characteristic of this promoter (Joseffson et al., 1987). Thus, one of the 35S antisense lines had a slightly diminished BNF5H transcript level whereas all of the Napin-Sense lines had a very high level in the seeds. The inventors of the present invention then examined the level of BNF5H polypeptide in the 35S antisense BNF5H1 transgenics by immunoblot analysis of crude extracts. The stem tissue of the 35S antisense BNF5H1 transgenic plants (except Line B1) showed lower levels of F5H polypeptide than the vector-transformed plants (FIG. 20). Immunoblot analyses of the seed extracts from the wild-type or vector-alone transgenic lines did not identify a clearly visible polypeptide corresponding to the one found in stem tissue, indicating that its presence in the seeds is at the detection limit of this method (data not shown). While the seeds from the Napin-sense lines contained a very high level of BNF5H transcript, there was no detectable increase in the BNF5H polypeptide.

Figure 21:
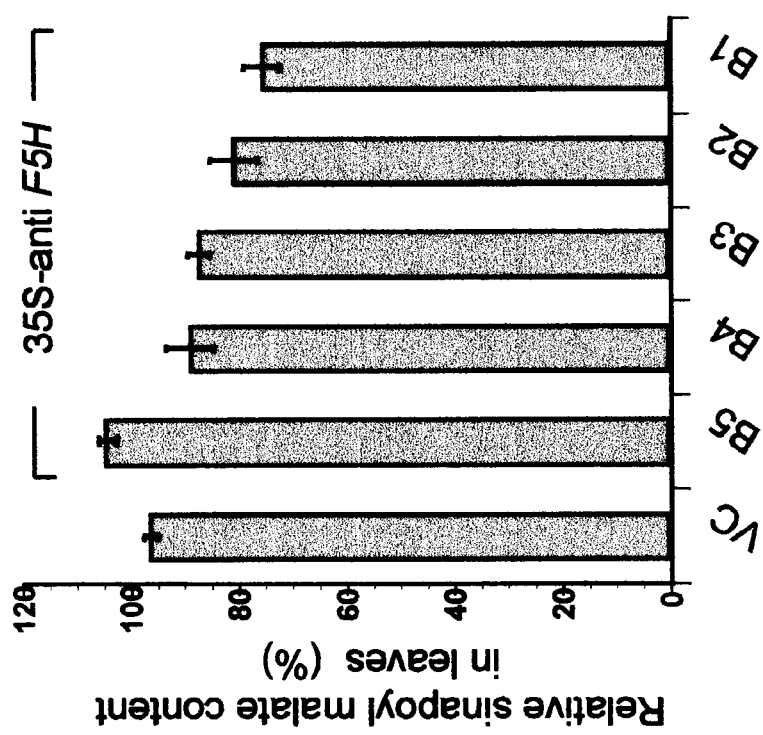
FIG. 21 shows a HPLC analysis of the sinapoyl malate content of the leaves from CaMV35S-antisense BNF5H1 (shown in the illustration as 35S anti F5H) transgenic lines. Three replications were done for each transgenic line. The average of sinapoyl malate content in the homozygous vector control leaves was taken as 100% for the relative values shown.

All of the $T_2$ plants were normal for their vegetative and reproductive phases of growth in a controlled cabinet. *B. napus* leaves contain a sinapoylmalate synthase activity, which is implicated in the synthesis of sinapoyl malate from sinapate derived precursors (Strack et al., 1990). Thus the 35S antisense F5H lines should show a reduction in the sinapoyl malate content if the BNF5H gene product(s) were involved in the biosynthesis of sinapate. The inventors of the present invention found a reduction in the sinapoyl malate content of the $T_2$ plants by up to 25%, relative to the vector-alone transgenics (FIG. 21).

DEPOSITS OF BIOLOGICAL MATERIALS

Vectors containing cDNA sequences according to the invention were deposited on behalf of the assignee of the present application at the International Depositary Authority of Canada, 1015 Arlington Street, Winnipeg, Manitoba, Canada, R3E 3R2, under the terms of the Budapest Treaty on May 2, 2000. The Authority has assigned the following Accession number(s) to the deposit(s): IDAC 020500-1; IDAC 020500-2; IDAC 020500-3; and IDAC 020500-4.

pJOY42, pJOY43 and pJOY44 plasmid, in Agrobacterium GV3101 used for *B. napus* transformation and pRAM5 used for F5H protein expression were also, deposited on behalf of the assignee of the present application at the International Depository Authority of Canada, 1015 Arlington Street, Winnipeg, Manitoba, Canada, R3E 3R2, under the terms of the Budapest Treaty on May 2, 2000. The Authority has assigned the following Accession number(s) to the deposit (s): IDAC 020500-5; IDAC 020500-6; IDAC 020500-7.

SEQUENCE LISTING

```
<160> NUMBER OF SEQ ID NOS:  22

<210> SEQ ID NO 1
<211> LENGTH: 1880
<212> TYPE: DNA
<213> ORGANISM: Brassica napus
<220> FEATURE:
<221> NAME/KEY: CDS
<222> LOCATION: (39)..(1598)

<400> SEQUENCE: 1
ataaaaaaac attttccaga aaaaaagaa aaactaat atg gag tct tct ata tca        56
                                         Met Glu Ser Ser Ile Ser
                                          1               5 caa aca cta agc caa gta ata gat ccc acc acg ggt att ctc atc gtc       104
Gln Thr Leu Ser Gln Val Ile Asp Pro Thr Thr Gly Ile Leu Ile Val
             10                  15                  20 gtc tca ctt ttc atc ttc atc ggc ctc atc aca cga cga cga agg cct       152
Val Ser Leu Phe Ile Phe Ile Gly Leu Ile Thr Arg Arg Arg Arg Pro
         25                  30                  35 ccg tat cca ccc ggt cca cgt ggt tgg ccc atc ata ggc aat atg tca       200
Pro Tyr Pro Pro Gly Pro Arg Gly Trp Pro Ile Ile Gly Asn Met Ser
     40                  45                  50 atg atg gac caa ctc acc cac cgt ggt tta gcc aac tta gct aaa aag       248
Met Met Asp Gln Leu Thr His Arg Gly Leu Ala Asn Leu Ala Lys Lys
 55                  60                  65                  70 tac ggt ggc ttg tgc cat ctc cgc atg gga ttt ctc cac atg tac gcc       296
Tyr Gly Gly Leu Cys His Leu Arg Met Gly Phe Leu His Met Tyr Ala
                 75                  80                  85 gtt tca tca cca gac gtg gct aaa caa gtc ctt caa gtc caa gac agc       344
Val Ser Ser Pro Asp Val Ala Lys Gln Val Leu Gln Val Gln Asp Ser
             90                  95                 100 gtc ttc tcg aac cga cca gct act ata gct ata agc tat ttg act tat       392
Val Phe Ser Asn Arg Pro Ala Thr Ile Ala Ile Ser Tyr Leu Thr Tyr
        105                 110                 115 gac cga gcc gac atg gcg ttt gct cac tac gga ccg ttt tgg aga cag       440
Asp Arg Ala Asp Met Ala Phe Ala His Tyr Gly Pro Phe Trp Arg Gln
    120                 125                 130 atg agg aaa gtt tgc gtc atg aag gtg ttt agc cgt aaa cga gcc gag       488
Met Arg Lys Val Cys Val Met Lys Val Phe Ser Arg Lys Arg Ala Glu
135                 140                 145                 150 tca tgg gct tct gtt cgt gat gaa gtg gac aaa atg atc cgg tcg gtt       536
Ser Trp Ala Ser Val Arg Asp Glu Val Asp Lys Met Ile Arg Ser Val
                155                 160                 165 tct agt aac gtt ggt aag tct atc aac gtt ggt gag caa att ttt gca       584
Ser Ser Asn Val Gly Lys Ser Ile Asn Val Gly Glu Gln Ile Phe Ala
            170                 175                 180 ctg acc cga aac ata act tac cgg gca gcg ttc ggg tca gca tgt gaa       632
Leu Thr Arg Asn Ile Thr Tyr Arg Ala Ala Phe Gly Ser Ala Cys Glu
        185                 190                 195
```

```
aag gga caa gac gag ttc ata aga att tta caa gag ttc tct aag ctt       680
Lys Gly Gln Asp Glu Phe Ile Arg Ile Leu Gln Glu Phe Ser Lys Leu
    200                 205                 210 ttt gga gcc ttc aac gta gcg gat ttc ata ccg tat ttc ggg tgg atc       728
Phe Gly Ala Phe Asn Val Ala Asp Phe Ile Pro Tyr Phe Gly Trp Ile
215                 220                 225                 230 gat cct caa gga ata aac aag cgg ctc gtg aag gcc cgt aat gac cta       776
Asp Pro Gln Gly Ile Asn Lys Arg Leu Val Lys Ala Arg Asn Asp Leu
                235                 240                 245 gac gga ttt att gac gat atc atc gat gaa cac atg aag aag aaa gag       824
Asp Gly Phe Ile Asp Asp Ile Ile Asp Glu His Met Lys Lys Lys Glu
            250                 255                 260 aat caa aac agt gtt gat gct gga gat gtt gtt gat acc gat atg gtt       872
Asn Gln Asn Ser Val Asp Ala Gly Asp Val Val Asp Thr Asp Met Val
        265                 270                 275 gat gat ctt ctt gct ttt tac agt gaa gag gcg aaa tta gtg agc gag       920
Asp Asp Leu Leu Ala Phe Tyr Ser Glu Glu Ala Lys Leu Val Ser Glu
    280                 285                 290 aca gcg gat ctt cag aac tct atc aaa ctt acc cgt gac aat atc aaa       968
Thr Ala Asp Leu Gln Asn Ser Ile Lys Leu Thr Arg Asp Asn Ile Lys
295                 300                 305                 310 gca atc atc atg gac gtt atg ttt gga gga acg gaa acg gta gcg tca      1016
Ala Ile Ile Met Asp Val Met Phe Gly Gly Thr Glu Thr Val Ala Ser
                315                 320                 325 gcg ata gag tgg gca ttg act gaa tta cta cgg agc ccc gag gat cta      1064
Ala Ile Glu Trp Ala Leu Thr Glu Leu Leu Arg Ser Pro Glu Asp Leu
            330                 335                 340 aac cga gtc caa caa gaa ctc gct gaa gtc gtc gga ctt gac cga cgt      1112
Asn Arg Val Gln Gln Glu Leu Ala Glu Val Val Gly Leu Asp Arg Arg
        345                 350                 355 gtg gaa gaa tca gac atc gag aag ttg act ttt ctg aaa tgc aca ctc      1160
Val Glu Glu Ser Asp Ile Glu Lys Leu Thr Phe Leu Lys Cys Thr Leu
    360                 365                 370 aaa gaa acc cta agg cta cac cca ccg atc cca ctc ctc cta cac gaa      1208
Lys Glu Thr Leu Arg Leu His Pro Pro Ile Pro Leu Leu Leu His Glu
375                 380                 385                 390 acc gca gag gac act gag atc gac ggt tac ttc gtt ccc aag aaa tct      1256
Thr Ala Glu Asp Thr Glu Ile Asp Gly Tyr Phe Val Pro Lys Lys Ser
                395                 400                 405 cgc gtt atg atc aac gcg ttt gcg att ggg cgc gac aag aac tct tgg      1304
Arg Val Met Ile Asn Ala Phe Ala Ile Gly Arg Asp Lys Asn Ser Trp
            410                 415                 420 gtt gac ccc gaa acg ttt aga ccg tct agg ttt ttg gaa ccg ggc gta      1352
Val Asp Pro Glu Thr Phe Arg Pro Ser Arg Phe Leu Glu Pro Gly Val
        425                 430                 435 cca gat ttc aaa ggg agt aac ttc gag ttt ata cca ttc ggg tcg ggt      1400
Pro Asp Phe Lys Gly Ser Asn Phe Glu Phe Ile Pro Phe Gly Ser Gly
    440                 445                 450 cgt agg tcg tgc ccg ggt atg caa ctc ggg tta tac gcg ctt gaa cta      1448
Arg Arg Ser Cys Pro Gly Met Gln Leu Gly Leu Tyr Ala Leu Glu Leu
455                 460                 465                 470 gcc gtg gcc cat ata tta cat tgc ttc acg tgg aaa tta cct gat ggc      1496
Ala Val Ala His Ile Leu His Cys Phe Thr Trp Lys Leu Pro Asp Gly
                475                 480                 485 atg aaa cca agc gag ctt gat atg agc gac gtg ttt ggt ctg acg gct      1544
Met Lys Pro Ser Glu Leu Asp Met Ser Asp Val Phe Gly Leu Thr Ala
            490                 495                 500 cct aaa gcc acg cgt ctc tat gct gtc ccg agc acg cgc ctt att tgt      1592
Pro Lys Ala Thr Arg Leu Tyr Ala Val Pro Ser Thr Arg Leu Ile Cys
```

```
                505                 510                 515
tct gtt taagttatgg ttcgaagcac gtggcgggtg aaaggaaagg tggttggtat           1648
Ser Val
    520 ggttcttgaa agtggtgtga gaagtcaaaa gaagccctga agatttgtgg atgttatata      1708 taatatatgt ttatgtattt gtgtgttcac acgtgtgttc tggatgaaac ataaagtggc      1768 tctttgtttc gttttccaat ttcttttgtg ggaattcttt tccttgcatg aaatgtaaac      1828 gctgaaaaat aagattttt tttacaacta aaaaaaaaaa aaaaaaaaaa aa               1880

<210> SEQ ID NO 2
<211> LENGTH: 520
<212> TYPE: PRT
<213> ORGANISM: Brassica napus

<400> SEQUENCE: 2

Met Glu Ser Ser Ile Ser Gln Thr Leu Ser Gln Val Ile Asp Pro Thr
  1               5                  10                  15

Thr Gly Ile Leu Ile Val Ser Leu Phe Ile Phe Ile Gly Leu Ile
             20                  25                  30

Thr Arg Arg Arg Arg Pro Pro Tyr Pro Pro Gly Pro Arg Gly Trp Pro
             35                  40                  45

Ile Ile Gly Asn Met Ser Met Met Asp Gln Leu Thr His Arg Gly Leu
 50                  55                  60

Ala Asn Leu Ala Lys Lys Tyr Gly Gly Leu Cys His Leu Arg Met Gly
 65                  70                  75                  80

Phe Leu His Met Tyr Ala Val Ser Ser Pro Asp Val Ala Lys Gln Val
                 85                  90                  95

Leu Gln Val Gln Asp Ser Val Phe Ser Asn Arg Pro Ala Thr Ile Ala
            100                 105                 110

Ile Ser Tyr Leu Thr Tyr Asp Arg Ala Asp Met Ala Phe Ala His Tyr
            115                 120                 125

Gly Pro Phe Trp Arg Gln Met Arg Lys Val Cys Val Met Lys Val Phe
        130                 135                 140

Ser Arg Lys Arg Ala Glu Ser Trp Ala Ser Val Arg Asp Glu Val Asp
145                 150                 155                 160

Lys Met Ile Arg Ser Val Ser Ser Asn Val Gly Lys Ser Ile Asn Val
                165                 170                 175

Gly Glu Gln Ile Phe Ala Leu Thr Arg Asn Ile Thr Tyr Arg Ala Ala
            180                 185                 190

Phe Gly Ser Ala Cys Glu Lys Gly Gln Asp Glu Phe Ile Arg Ile Leu
        195                 200                 205

Gln Glu Phe Ser Lys Leu Phe Gly Ala Phe Asn Val Ala Asp Phe Ile
    210                 215                 220

Pro Tyr Phe Gly Trp Ile Asp Pro Gln Gly Ile Asn Lys Arg Leu Val
225                 230                 235                 240

Lys Ala Arg Asn Asp Leu Asp Gly Phe Ile Asp Asp Ile Ile Asp Glu
                245                 250                 255

His Met Lys Lys Lys Glu Asn Gln Asn Ser Val Asp Ala Gly Asp Val
            260                 265                 270

Val Asp Thr Asp Met Val Asp Leu Leu Ala Phe Tyr Ser Glu Glu
        275                 280                 285

Ala Lys Leu Val Ser Glu Thr Ala Asp Leu Gln Asn Ser Ile Lys Leu
    290                 295                 300
```

```
Thr Arg Asp Asn Ile Lys Ala Ile Ile Met Asp Val Met Phe Gly Gly
305                 310                 315                 320

Thr Glu Thr Val Ala Ser Ala Ile Glu Trp Ala Leu Thr Glu Leu Leu
            325                 330                 335

Arg Ser Pro Glu Asp Leu Asn Arg Val Gln Gln Glu Leu Ala Glu Val
                340                 345                 350

Val Gly Leu Asp Arg Arg Val Glu Glu Ser Asp Ile Glu Lys Leu Thr
            355                 360                 365

Phe Leu Lys Cys Thr Leu Lys Glu Thr Leu Arg Leu His Pro Pro Ile
        370                 375                 380

Pro Leu Leu Leu His Glu Thr Ala Glu Asp Thr Glu Ile Asp Gly Tyr
385                 390                 395                 400

Phe Val Pro Lys Lys Ser Arg Val Met Ile Asn Ala Phe Ala Ile Gly
                405                 410                 415

Arg Asp Lys Asn Ser Trp Val Asp Pro Glu Thr Phe Arg Pro Ser Arg
            420                 425                 430

Phe Leu Glu Pro Gly Val Pro Asp Phe Lys Gly Ser Asn Phe Glu Phe
        435                 440                 445

Ile Pro Phe Gly Ser Gly Arg Arg Ser Cys Pro Gly Met Gln Leu Gly
    450                 455                 460

Leu Tyr Ala Leu Glu Leu Ala Val Ala His Ile Leu His Cys Phe Thr
465                 470                 475                 480

Trp Lys Leu Pro Asp Gly Met Lys Pro Ser Glu Leu Asp Met Ser Asp
                485                 490                 495

Val Phe Gly Leu Thr Ala Pro Lys Ala Thr Arg Leu Tyr Ala Val Pro
            500                 505                 510

Ser Thr Arg Leu Ile Cys Ser Val
        515                 520

<210> SEQ ID NO 3
<211> LENGTH: 1884
<212> TYPE: DNA
<213> ORGANISM: Brassica napus
<220> FEATURE:
<221> NAME/KEY: CDS
<222> LOCATION: (52)..(1611)

<400> SEQUENCE: 3
accttccaca acaatagaa aaaacatttc ccagaaaaaa gaaaaactaa t atg gag        57
                                                        Met Glu
                                                          1 tct tct ata tca caa aca cta agc caa gta tta gat ccc acc acg ggt      105
Ser Ser Ile Ser Gln Thr Leu Ser Gln Val Leu Asp Pro Thr Thr Gly
        5                  10                  15 att ctc atc gtt gtc tca ctt ttc atc ttc atc ggc ctc atc aca cgg    153
Ile Leu Ile Val Val Ser Leu Phe Ile Phe Ile Gly Leu Ile Thr Arg
 20                  25                  30 cga cga agg cct ccg tac cca ccc ggt cca cgt ggt tgg ccc atc ata    201
Arg Arg Arg Pro Pro Tyr Pro Pro Gly Pro Arg Gly Trp Pro Ile Ile
 35                  40                  45                  50 ggc aat atg tca atg atg gac caa ctc act cac cgt ggt tta gcc aac    249
Gly Asn Met Ser Met Met Asp Gln Leu Thr His Arg Gly Leu Ala Asn
                 55                  60                  65 tta gct aaa aag tac ggt ggc ctg tgc cat ctc cgc atg gga ttt ctc    297
Leu Ala Lys Lys Tyr Gly Gly Leu Cys His Leu Arg Met Gly Phe Leu
         70                  75                  80 cac atg tac gcc gtt tcc tcg cca gac gtg gct aag caa gtc ctt caa    345
His Met Tyr Ala Val Ser Ser Pro Asp Val Ala Lys Gln Val Leu Gln
```

-continued

|   |   |   |   | 85 |   |   |   |   | 90 |   |   |   |   | 95 |   |   |
|---|---|---|---|---|---|---|---|---|---|---|---|---|---|---|---|---|

```
gtc cag gac agc gtc ttc tca aac cga cca gca act ata gct ata agc      393
Val Gln Asp Ser Val Phe Ser Asn Arg Pro Ala Thr Ile Ala Ile Ser
    100                 105                 110 tat ttg act tat gac cga gcc gac atg gcg ttt gct cac tac gga ccg      441
Tyr Leu Thr Tyr Asp Arg Ala Asp Met Ala Phe Ala His Tyr Gly Pro
115                 120                 125                 130 ttt tgg aga cag atg agg aaa gtt tgt gtc atg aag gtg ttt agc cgt      489
Phe Trp Arg Gln Met Arg Lys Val Cys Val Met Lys Val Phe Ser Arg
                135                 140                 145 aaa cga gcc gag tca tgg gct tct gtt cgt gat gaa gtg gac aaa atg      537
Lys Arg Ala Glu Ser Trp Ala Ser Val Arg Asp Glu Val Asp Lys Met
            150                 155                 160 atc cgg tcg gtt tct agt aac gtt ggt aag tct atc aac gtt ggt gag      585
Ile Arg Ser Val Ser Ser Asn Val Gly Lys Ser Ile Asn Val Gly Glu
        165                 170                 175 caa att ttt gca ctg acc cga aac ata act tac cgg gca gcg ttc ggg      633
Gln Ile Phe Ala Leu Thr Arg Asn Ile Thr Tyr Arg Ala Ala Phe Gly
    180                 185                 190 tca gca tgt gaa aag gga caa gac gag ttc ata aga att tta caa gag      681
Ser Ala Cys Glu Lys Gly Gln Asp Glu Phe Ile Arg Ile Leu Gln Glu
195                 200                 205                 210 ttc tct aag ctt ttt gga gcc ttc aac gta gcg gat ttc ata ccg tat      729
Phe Ser Lys Leu Phe Gly Ala Phe Asn Val Ala Asp Phe Ile Pro Tyr
                215                 220                 225 ttc ggg tgg atc gat ccg caa gga ata aac aag cgg ctc gtg aag gcc      777
Phe Gly Trp Ile Asp Pro Gln Gly Ile Asn Lys Arg Leu Val Lys Ala
            230                 235                 240 cgt aat gac cta gac gga ttt att gac gat atc atc gat gaa cac ata      825
Arg Asn Asp Leu Asp Gly Phe Ile Asp Asp Ile Ile Asp Glu His Ile
        245                 250                 255 aag aag aaa gag aat caa aac agt gtt gat gct gga gat gtt gtt gat      873
Lys Lys Lys Glu Asn Gln Asn Ser Val Asp Ala Gly Asp Val Val Asp
    260                 265                 270 acc gat atg gtt gat gat ctt ctt gct ttt tac agt gaa gag gcg aaa      921
Thr Asp Met Val Asp Asp Leu Leu Ala Phe Tyr Ser Glu Glu Ala Lys
275                 280                 285                 290 tta gtg agc gag aca gcg gat ctt cag aac tcc atc aaa ctt acc cgt      969
Leu Val Ser Glu Thr Ala Asp Leu Gln Asn Ser Ile Lys Leu Thr Arg
                295                 300                 305 gac aat atc aaa gca atc atc atg gac gtt atg ttt gga gga acg gaa     1017
Asp Asn Ile Lys Ala Ile Ile Met Asp Val Met Phe Gly Gly Thr Glu
            310                 315                 320 acg gta gcg tca gcg ata gag tgg gca ttg act gag tta tta cgg agc     1065
Thr Val Ala Ser Ala Ile Glu Trp Ala Leu Thr Glu Leu Leu Arg Ser
        325                 330                 335 cca gag gat cta aaa cga gtc caa caa gaa ctc gct gaa gtt gtc gga     1113
Pro Glu Asp Leu Lys Arg Val Gln Gln Glu Leu Ala Glu Val Val Gly
    340                 345                 350 ctt gac cga cgt gtg gaa gaa tca gac atc gag aag ttg act ttt ttg     1161
Leu Asp Arg Arg Val Glu Glu Ser Asp Ile Glu Lys Leu Thr Phe Leu
355                 360                 365                 370 aaa tgc aca ctc aat gaa acc cta agg cta cac cca ccg atc cca ctc     1209
Lys Cys Thr Leu Asn Glu Thr Leu Arg Leu His Pro Pro Ile Pro Leu
                375                 380                 385 ctc ctc cac gaa acc gca gag gac act gag atc gac ggt tac ttc gtt     1257
Leu Leu His Glu Thr Ala Glu Asp Thr Glu Ile Asp Gly Tyr Phe Val
            390                 395                 400 ccc aag aaa tct cgc gtt atg atc aac gcg ttt gcg att gga cgc gac     1305
```

```
                      Pro Lys Lys Ser Arg Val Met Ile Asn Ala Phe Ala Ile Gly Arg Asp
                              405                 410                 415 aag aac tct tgg gtt gat ccc gaa acg ttt aga ccg tcc agg ttt ttg         1353
Lys Asn Ser Trp Val Asp Pro Glu Thr Phe Arg Pro Ser Arg Phe Leu
420                 425                 430 gaa ccg ggc gta cca gat ttc aaa ggg agt aac ttc gag ttt ata cca         1401
Glu Pro Gly Val Pro Asp Phe Lys Gly Ser Asn Phe Glu Phe Ile Pro
435                 440                 445                 450 ttc ggg tcg ggt cgt cgg tcg tgc ccg ggt atg cag ctc ggg tta tac         1449
Phe Gly Ser Gly Arg Arg Ser Cys Pro Gly Met Gln Leu Gly Leu Tyr
                455                 460                 465 gcg ctt gaa cta gcc gtg gcc cat ata tta cat tgc ttc acg tgg aaa         1497
Ala Leu Glu Leu Ala Val Ala His Ile Leu His Cys Phe Thr Trp Lys
            470                 475                 480 tta cct gat ggc atg aaa cca agc gag ctt gat atg agc gac gtg ttt         1545
Leu Pro Asp Gly Met Lys Pro Ser Glu Leu Asp Met Ser Asp Val Phe
        485                 490                 495 ggt ctg acg gct cct aaa gcc acg cgt ctc tac gct gtc ccg tgc acg         1593
Gly Leu Thr Ala Pro Lys Ala Thr Arg Leu Tyr Ala Val Pro Cys Thr
    500                 505                 510 cgc ctt att tgt tct gtt taagttatgg ttcgaaacac gtggcgggtg                1641
Arg Leu Ile Cys Ser Val
515                 520 aaatgaaagg tggttggtat ggttgatggt tcttgaaagt ggtgtgagaa gtcaaacgaa       1701
gccctgaaaa tttgtggatg ttatataata ctatatgttt atgtatttgt tgtgtacacg       1761
tacacacgtg tgttctggat gaaacataaa gtggctcttt atttcgtttt tcatcttctt       1821
ttgtgggaat tttttccttg catgaaatgt aaacgctgaa aataagatt ttttttttaca       1881 act                                                                     1884

<210> SEQ ID NO 4
<211> LENGTH: 520
<212> TYPE: PRT
<213> ORGANISM: Brassica napus

<400> SEQUENCE: 4

Met Glu Ser Ser Ile Ser Gln Thr Leu Ser Gln Val Leu Asp Pro Thr
1               5                   10                  15

Thr Gly Ile Leu Ile Val Ser Leu Phe Ile Phe Ile Gly Leu Ile
                20                  25                  30

Thr Arg Arg Arg Pro Pro Tyr Pro Pro Gly Pro Arg Gly Trp Pro
            35                  40                  45

Ile Ile Gly Asn Met Ser Met Met Asp Gln Leu Thr His Arg Gly Leu
    50                  55                  60

Ala Asn Leu Ala Lys Lys Tyr Gly Gly Leu Cys His Leu Arg Met Gly
65                  70                  75                  80

Phe Leu His Met Tyr Ala Val Ser Ser Pro Asp Val Ala Lys Gln Val
                85                  90                  95

Leu Gln Val Gln Asp Ser Val Phe Ser Asn Arg Pro Ala Thr Ile Ala
                100                 105                 110

Ile Ser Tyr Leu Thr Tyr Asp Arg Ala Asp Met Ala Phe Ala His Tyr
            115                 120                 125

Gly Pro Phe Trp Arg Gln Met Arg Lys Val Cys Val Met Lys Val Phe
    130                 135                 140

Ser Arg Lys Arg Ala Glu Ser Trp Ala Ser Val Arg Asp Glu Val Asp
145                 150                 155                 160
```

-continued

```
Lys Met Ile Arg Ser Val Ser Asn Val Gly Lys Ser Ile Asn Val
            165                 170                 175

Gly Glu Gln Ile Phe Ala Leu Thr Arg Asn Ile Thr Tyr Arg Ala Ala
            180                 185                 190

Phe Gly Ser Ala Cys Glu Lys Gly Gln Asp Glu Phe Ile Arg Ile Leu
            195                 200                 205

Gln Glu Phe Ser Lys Leu Phe Gly Ala Phe Asn Val Ala Asp Phe Ile
    210                 215                 220

Pro Tyr Phe Gly Trp Ile Asp Pro Gln Gly Ile Asn Lys Arg Leu Val
225                 230                 235                 240

Lys Ala Arg Asn Asp Leu Asp Gly Phe Ile Asp Ile Ile Asp Glu
            245                 250                 255

His Ile Lys Lys Lys Glu Asn Gln Asn Ser Val Asp Ala Gly Asp Val
            260                 265                 270

Val Asp Thr Asp Met Val Asp Asp Leu Leu Ala Phe Tyr Ser Glu Glu
            275                 280                 285

Ala Lys Leu Val Ser Glu Thr Ala Asp Leu Gln Asn Ser Ile Lys Leu
            290                 295                 300

Thr Arg Asp Asn Ile Lys Ala Ile Ile Met Asp Val Met Phe Gly Gly
305                 310                 315                 320

Thr Glu Thr Val Ala Ser Ala Ile Glu Trp Ala Leu Thr Glu Leu Leu
            325                 330                 335

Arg Ser Pro Glu Asp Leu Lys Arg Val Gln Gln Glu Leu Ala Glu Val
            340                 345                 350

Val Gly Leu Asp Arg Arg Val Glu Glu Ser Asp Ile Glu Lys Leu Thr
            355                 360                 365

Phe Leu Lys Cys Thr Leu Asn Glu Thr Leu Arg Leu His Pro Pro Ile
    370                 375                 380

Pro Leu Leu Leu His Glu Thr Ala Glu Asp Thr Glu Ile Asp Gly Tyr
385                 390                 395                 400

Phe Val Pro Lys Lys Ser Arg Val Met Ile Asn Ala Phe Ala Ile Gly
            405                 410                 415

Arg Asp Lys Asn Ser Trp Val Asp Pro Glu Thr Phe Arg Pro Ser Arg
            420                 425                 430

Phe Leu Glu Pro Gly Val Pro Asp Phe Lys Gly Ser Asn Phe Glu Phe
            435                 440                 445

Ile Pro Phe Gly Ser Gly Arg Arg Ser Cys Pro Gly Met Gln Leu Gly
    450                 455                 460

Leu Tyr Ala Leu Glu Leu Ala Val Ala His Ile Leu His Cys Phe Thr
465                 470                 475                 480

Trp Lys Leu Pro Asp Gly Met Lys Pro Ser Glu Leu Asp Met Ser Asp
            485                 490                 495

Val Phe Gly Leu Thr Ala Pro Lys Ala Thr Arg Leu Tyr Ala Val Pro
            500                 505                 510

Cys Thr Arg Leu Ile Cys Ser Val
            515                 520

<210> SEQ ID NO 5
<211> LENGTH: 1835
<212> TYPE: DNA
<213> ORGANISM: Brassica napus
<220> FEATURE:
<221> NAME/KEY: CDS
<222> LOCATION: (2)..(1540)

<400> SEQUENCE: 5
```

```
a caa aca cta agt caa tta tta gat ccc aca acg gct att ctc atc atc      49
  Gln Thr Leu Ser Gln Leu Leu Asp Pro Thr Thr Ala Ile Leu Ile Ile
   1               5                  10                  15 gtc tca ctt ttc ata ttc atc ggc ctc atc aca cga cgg cga agg tct        97
Val Ser Leu Phe Ile Phe Ile Gly Leu Ile Thr Arg Arg Arg Arg Ser
            20                  25                  30 tac cca ccc ggt cca cgt ggt tgg ccc atc ata ggc aat atg tta atg       145
Tyr Pro Pro Gly Pro Arg Gly Trp Pro Ile Ile Gly Asn Met Leu Met
        35                  40                  45 atg gac caa ctc acc cac cgt ggt tta gcc aac tta gct aaa aaa tat       193
Met Asp Gln Leu Thr His Arg Gly Leu Ala Asn Leu Ala Lys Lys Tyr
 50                  55                  60 ggc ggc ttg tgc cat ctc cgc atg ggc ttc ctc cat atg tat gcc gtc       241
Gly Gly Leu Cys His Leu Arg Met Gly Phe Leu His Met Tyr Ala Val
 65                  70                  75                  80 tca tca cct cat gtg gct cga caa gtc ctc caa gtc caa gac agc atc       289
Ser Ser Pro His Val Ala Arg Gln Val Leu Gln Val Gln Asp Ser Ile
                85                  90                  95 ttc tcg aac cgg ccg gca acg ata gct ata agc tat ttg act tat gac       337
Phe Ser Asn Arg Pro Ala Thr Ile Ala Ile Ser Tyr Leu Thr Tyr Asp
           100                 105                 110 cga gcc gac atg gcg ttc gct cac tac gga ccg ttt tgg aga cag atg       385
Arg Ala Asp Met Ala Phe Ala His Tyr Gly Pro Phe Trp Arg Gln Met
       115                 120                 125 agg aaa gtg tgt gtc atg aag gtg ttt agc cgt aaa cgt gcg gag tca       433
Arg Lys Val Cys Val Met Lys Val Phe Ser Arg Lys Arg Ala Glu Ser
   130                 135                 140 tgg gct tct gtt cga gat gaa gtg gac aaa atg atc cgg tcg gta tct       481
Trp Ala Ser Val Arg Asp Glu Val Asp Lys Met Ile Arg Ser Val Ser
145                 150                 155                 160 agt aac gtt ggt aag tct ata aac gtc ggg gag caa att ttc gcc ctg       529
Ser Asn Val Gly Lys Ser Ile Asn Val Gly Glu Gln Ile Phe Ala Leu
               165                 170                 175 acc cga aac ata act tac cgg gca gcg ttc ggg tca gct tgc gaa aag       577
Thr Arg Asn Ile Thr Tyr Arg Ala Ala Phe Gly Ser Ala Cys Glu Lys
           180                 185                 190 gga caa gat gag ttc ata aga atc tta caa gag ttc tct aag ctt ttt       625
Gly Gln Asp Glu Phe Ile Arg Ile Leu Gln Glu Phe Ser Lys Leu Phe
       195                 200                 205 gga gcc ttc aac gta gca gat ttc ata cca tat ttt ggg tgg atc gat       673
Gly Ala Phe Asn Val Ala Asp Phe Ile Pro Tyr Phe Gly Trp Ile Asp
   210                 215                 220 cca caa ggg ata agc aag cgg ctc gtg aag gcc cgt aat gat cta gac       721
Pro Gln Gly Ile Ser Lys Arg Leu Val Lys Ala Arg Asn Asp Leu Asp
225                 230                 235                 240 gga ttt att gac gat atc atc gac gaa cat atg aag aag aaa gag aat       769
Gly Phe Ile Asp Asp Ile Ile Asp Glu His Met Lys Lys Lys Glu Asn
               245                 250                 255 caa aac act gtt gat gat gga gat gtt ggt gat acc gat atg gtt gat       817
Gln Asn Thr Val Asp Asp Gly Asp Val Gly Asp Thr Asp Met Val Asp
           260                 265                 270 gat ctt ctt gct ttt tac agt gaa gag gcc aaa tta gtg agc gag aca       865
Asp Leu Leu Ala Phe Tyr Ser Glu Glu Ala Lys Leu Val Ser Glu Thr
       275                 280                 285 acg gat ctt cag aat tct atc aaa ctt acc cgt gac aat atc aaa gca       913
Thr Asp Leu Gln Asn Ser Ile Lys Leu Thr Arg Asp Asn Ile Lys Ala
   290                 295                 300 atc atc atg gac gtc atg ttc gga gga acg gaa acg gta gct tct gca       961
Ile Ile Met Asp Val Met Phe Gly Gly Thr Glu Thr Val Ala Ser Ala
```

-continued

```
305                 310                 315                 320
ata gag tgg gcc tta acg gag tta tta cgg agc ccc gag gat cta aaa    1009
Ile Glu Trp Ala Leu Thr Glu Leu Leu Arg Ser Pro Glu Asp Leu Lys
                325                 330                 335 cgg gtc caa caa gaa ctc gct gaa gtt gtc gga ctt gac cga cgt gtg    1057
Arg Val Gln Gln Glu Leu Ala Glu Val Val Gly Leu Asp Arg Arg Val
            340                 345                 350 gaa gaa tca gac atc gag aag ttg act ttt ctg aaa tgc aca ctc aaa    1105
Glu Glu Ser Asp Ile Glu Lys Leu Thr Phe Leu Lys Cys Thr Leu Lys
        355                 360                 365 gaa acc cta agg tta cac cca ccg atc cca ctc ctc ctc cac gaa acc    1153
Glu Thr Leu Arg Leu His Pro Pro Ile Pro Leu Leu Leu His Glu Thr
    370                 375                 380 gca gag gac act gag atc gac ggt tac ttc gtt ccc aag aaa tcg cgc    1201
Ala Glu Asp Thr Glu Ile Asp Gly Tyr Phe Val Pro Lys Lys Ser Arg
385                 390                 395                 400 gtt atg atc aac gcg ttt gcc att gga cgt gac cct aaa tct tgg cct    1249
Val Met Ile Asn Ala Phe Ala Ile Gly Arg Asp Pro Lys Ser Trp Pro
                405                 410                 415 gac gcc gaa acg ttt aga ccg tcg agg ttt tta gaa ccg gga gta gcg    1297
Asp Ala Glu Thr Phe Arg Pro Ser Arg Phe Leu Glu Pro Gly Val Ala
            420                 425                 430 gat ttc aaa gga agt aac ttc gag ttt ata cca ttc ggg tcg ggt cgt    1345
Asp Phe Lys Gly Ser Asn Phe Glu Phe Ile Pro Phe Gly Ser Gly Arg
        435                 440                 445 aaa tcg tgc ccg ggt atg caa ctc ggg tta tac gcg ctt gag tta gcc    1393
Lys Ser Cys Pro Gly Met Gln Leu Gly Leu Tyr Ala Leu Glu Leu Ala
    450                 455                 460 gtt gct cat ata tta cat tgc ttc aca tgg aaa tta cct gat ggg atg    1441
Val Ala His Ile Leu His Cys Phe Thr Trp Lys Leu Pro Asp Gly Met
465                 470                 475                 480 aaa gcg agc gag ctt gac atg aac gac gtg ttt ggt ctc acg gct cct    1489
Lys Ala Ser Glu Leu Asp Met Asn Asp Val Phe Gly Leu Thr Ala Pro
                485                 490                 495 aaa gcc act cgt ctt ttc gcc gtg cct agc aca cgc ctg att tgt gct    1537
Lys Ala Thr Arg Leu Phe Ala Val Pro Ser Thr Arg Leu Ile Cys Ala
            500                 505                 510 gtc taagttattg ttcgtagcac gtggcgggtg taaaaccaaa cgaagggttg         1590
Val gtaataggta tggttcttgg aaagagtttg aaaagtcaaa tgtagcactg aacatttgtg  1650
gatgttatta tatgtatgta tgtgtatcac gtgtggtctg gatgaaaaca taaatggctc  1710
tttgtttcga ttttcctttt cttttgttgg gattttttcct tgaatgaaaa tgtaactggt 1770
aaaatatagt ttttttttat cttaaaaaaa aaaaaaaaaa aaaaaaaaaa aaaaaaaaaa  1830
aaaaa                                                              1835
```

<210> SEQ ID NO 6
<211> LENGTH: 513
<212> TYPE: PRT
<213> ORGANISM: Brassica napus

<400> SEQUENCE: 6

```
Gln Thr Leu Ser Gln Leu Leu Asp Pro Thr Thr Ala Ile Leu Ile Ile
  1               5                  10                  15

Val Ser Leu Phe Ile Phe Ile Gly Leu Ile Thr Arg Arg Arg Arg Ser
                 20                  25                  30

Tyr Pro Pro Gly Pro Arg Gly Trp Pro Ile Ile Gly Asn Met Leu Met
             35                  40                  45
```

-continued

```
Met Asp Gln Leu Thr His Arg Gly Leu Ala Asn Leu Ala Lys Lys Tyr
 50                      55                  60
Gly Gly Leu Cys His Leu Arg Met Gly Phe Leu His Met Tyr Ala Val
 65                  70                  75                  80
Ser Ser Pro His Val Ala Arg Gln Val Leu Gln Val Gln Asp Ser Ile
                 85                  90                  95
Phe Ser Asn Arg Pro Ala Thr Ile Ala Ile Ser Tyr Leu Thr Tyr Asp
                100                 105                 110
Arg Ala Asp Met Ala Phe Ala His Tyr Gly Pro Phe Trp Arg Gln Met
             115                 120                 125
Arg Lys Val Cys Val Met Lys Val Phe Ser Arg Lys Arg Ala Glu Ser
         130                 135                 140
Trp Ala Ser Val Arg Asp Glu Val Asp Lys Met Ile Arg Ser Val Ser
145                 150                 155                 160
Ser Asn Val Gly Lys Ser Ile Asn Val Gly Glu Gln Ile Phe Ala Leu
                165                 170                 175
Thr Arg Asn Ile Thr Tyr Arg Ala Ala Phe Gly Ser Ala Cys Glu Lys
             180                 185                 190
Gly Gln Asp Glu Phe Ile Arg Ile Leu Gln Glu Phe Ser Lys Leu Phe
         195                 200                 205
Gly Ala Phe Asn Val Ala Asp Phe Ile Pro Tyr Phe Gly Trp Ile Asp
210                 215                 220
Pro Gln Gly Ile Ser Lys Arg Leu Val Lys Ala Arg Asn Asp Leu Asp
225                 230                 235                 240
Gly Phe Ile Asp Asp Ile Ile Asp Glu His Met Lys Lys Lys Glu Asn
             245                 250                 255
Gln Asn Thr Val Asp Asp Gly Asp Val Gly Asp Thr Asp Met Val Asp
         260                 265                 270
Asp Leu Leu Ala Phe Tyr Ser Glu Glu Ala Lys Leu Val Ser Glu Thr
     275                 280                 285
Thr Asp Leu Gln Asn Ser Ile Lys Leu Thr Arg Asp Asn Ile Lys Ala
     290                 295                 300
Ile Ile Met Asp Val Met Phe Gly Gly Thr Glu Thr Val Ala Ser Ala
305                 310                 315                 320
Ile Glu Trp Ala Leu Thr Glu Leu Leu Arg Ser Pro Glu Asp Leu Lys
             325                 330                 335
Arg Val Gln Gln Glu Leu Ala Glu Val Val Gly Leu Asp Arg Arg Val
         340                 345                 350
Glu Glu Ser Asp Ile Glu Lys Leu Thr Phe Leu Lys Cys Thr Leu Lys
     355                 360                 365
Glu Thr Leu Arg Leu His Pro Pro Ile Pro Leu Leu His Glu Thr
     370                 375                 380
Ala Glu Asp Thr Glu Ile Asp Gly Tyr Phe Val Pro Lys Lys Ser Arg
385                 390                 395                 400
Val Met Ile Asn Ala Phe Ala Ile Gly Arg Asp Pro Lys Ser Trp Pro
             405                 410                 415
Asp Ala Glu Thr Phe Arg Pro Ser Arg Phe Leu Glu Pro Gly Val Ala
         420                 425                 430
Asp Phe Lys Gly Ser Asn Phe Glu Phe Ile Pro Phe Gly Ser Gly Arg
     435                 440                 445
Lys Ser Cys Pro Gly Met Gln Leu Gly Leu Tyr Ala Leu Glu Leu Ala
450                 455                 460
```

```
Val Ala His Ile Leu His Cys Phe Thr Trp Lys Leu Pro Asp Gly Met
465                 470                 475                 480

Lys Ala Ser Glu Leu Asp Met Asn Asp Val Phe Gly Leu Thr Ala Pro
                485                 490                 495

Lys Ala Thr Arg Leu Phe Ala Val Pro Ser Thr Arg Leu Ile Cys Ala
            500                 505                 510

Val

<210> SEQ ID NO 7
<211> LENGTH: 19
<212> TYPE: DNA
<213> ORGANISM: Brassica napus

<400> SEQUENCE: 7
cgagtcatgg gcttctgtt                                              19

<210> SEQ ID NO 8
<211> LENGTH: 21
<212> TYPE: DNA
<213> ORGANISM: Brassica napus

<400> SEQUENCE: 8
tatcgctgac gctaccgttc c                                           21

<210> SEQ ID NO 9
<211> LENGTH: 17
<212> TYPE: DNA
<213> ORGANISM: Brassica napus

<400> SEQUENCE: 9
agatgaggaa agtgtgt                                                17

<210> SEQ ID NO 10
<211> LENGTH: 19
<212> TYPE: DNA
<213> ORGANISM: Brassica napus

<400> SEQUENCE: 10
ccgtaataac tccgttaag                                              19

<210> SEQ ID NO 11
<211> LENGTH: 18
<212> TYPE: DNA
<213> ORGANISM: Brassica napus

<400> SEQUENCE: 11
ttctcgaacc gaccagct                                               18

<210> SEQ ID NO 12
<211> LENGTH: 18
<212> TYPE: DNA
<213> ORGANISM: Brassica napus

<400> SEQUENCE: 12
acaaataagg cgcgtgct                                               18

<210> SEQ ID NO 13
<211> LENGTH: 22
<212> TYPE: DNA
<213> ORGANISM: Brassica napus

<400> SEQUENCE: 13
```

-continued

```
gagtgggcat tgactgaatt ac                                    22

<210> SEQ ID NO 14
<211> LENGTH: 19
<212> TYPE: DNA
<213> ORGANISM: Brassica napus

<400> SEQUENCE: 14
ccataccaac cacctttcc                                         19

<210> SEQ ID NO 15
<211> LENGTH: 18
<212> TYPE: DNA
<213> ORGANISM: Brassica napus

<400> SEQUENCE: 15
gggcattgac tgagttat                                          18

<210> SEQ ID NO 16
<211> LENGTH: 19
<212> TYPE: DNA
<213> ORGANISM: Brassica napus

<400> SEQUENCE: 16
ccacagctca agaaccatc                                         19

<210> SEQ ID NO 17
<211> LENGTH: 24
<212> TYPE: DNA
<213> ORGANISM: Brassica napus

<400> SEQUENCE: 17
cgcgacaaga actcttgggt tgat                                   24

<210> SEQ ID NO 18
<211> LENGTH: 22
<212> TYPE: DNA
<213> ORGANISM: Brassica napus

<400> SEQUENCE: 18
ccacgttcaa gaaccatcaa cc                                     22

<210> SEQ ID NO 19
<211> LENGTH: 21
<212> TYPE: DNA
<213> ORGANISM: Brassica napus

<400> SEQUENCE: 19
accctaaatc ttggcctgac g                                      21

<210> SEQ ID NO 20
<211> LENGTH: 23
<212> TYPE: DNA
<213> ORGANISM: Brassica napus

<400> SEQUENCE: 20
ccatacctac taccaaccct tcg                                    23

<210> SEQ ID NO 21
<211> LENGTH: 17
<212> TYPE: DNA
<213> ORGANISM: Brassica napus

<400> SEQUENCE: 21
```

```
-continued ttagaaccgg gagtagc                                              17

<210> SEQ ID NO 22
<211> LENGTH: 18
<212> TYPE: DNA
<213> ORGANISM: Brassica napus

<400> SEQUENCE: 22
cctattacca acccttcg                                             18
```

REFERENCES

An G, Ebert P, Mitra A, Ha SB (1988) Binary vectors. In S B Gelvin, R A Schilperoot, eds, Plant Molecular Biology Manual, Kluwer Academic, Dordrecht, pp A3: 1–19.

Anderson J K, Warwick SI (1999) Chromosome number evolution in the tribe Brassiceae (Brassicaceae): Evidence from isozyme number. Plant Systematics and Evolution 215: 255–285

Bell J M (1993) Factors affecting the nutritional value of canola meal: A review. Can J Anim Sci 73: 679–697

Bell-Lelong D A, Cusumano J C, Meyer K, Chapple C (1997) Cinnamate-4-hydroxylase expression in Arabidopsis: Regulation in response to development and the environment. Plant Physiol 113: 729–738

Bouchereau A, Hamelin J, Lamour I, Renard M, Larher F (1991) Distribution of sinapine and related compounds in seeds of Brassica and allied genera. Phytochemistry 30: 1873–1881

Boudet A M, Lapierre C, Grima-Pettenati, J (1995) Biochemistry and molecular biology of lignification. New Phytol 129: 203–236

Bourque J E (1995) Antisense strategies for genetic manipulations in plants. Plant Sci 105: 125–149

Campbell M M, Sederoff R R (1996) Variation in lignin content and composition: Mechanisms of control and implications for the genetic improvement of plants. Plant Physiol 110: 3–13

Chapple C (1994) Genetic characterization of secondary metabolism in Arabidopsis. In B E Ellis, G W Kuroki, H A Stafford, eds, Genetic engineering of plant secondary metabolism. Plenum press, New York, pp 251–274

Chapple C C S and Ellis B E (1992) Secondary metabolite profiles of crucifer seeds:
biogenesis, role, and prospects for directed modification Curr Topics Plant Physiol 1992 7: 239–248

Chapple C, Vogt T, Ellis B E, Somerville C R (1992) An Arabidopsis mutant defective in the general phenylpropanoid pathway. Plant Cell 4: 1413–1424

Chen F, Yasuda S, Fukushima K (1999) Evidence for a novel biosynthetic pathway that regulates the ratio of syringyl to guaiacyl residues in lignin in the differentiating xylem of Magnolia kobus D C. Planta 207: 597–603

Cherney J H, Cherney D J R, Akin D E, Axtell J D 1991 Potential of brown-midrib, low lignin mutants for improving forage quality. Adv Agron 46: 157–198.

Datla R S S, Bekkaoui F, Hammerlindl J K, Pilate G, Dunstan D I, Crosby W L (1993) Improved high-level constitutive foreign gene expression in plants using an AMV RNA4 untranslated leader sequence. Plant Sci 94: 139–149

Datla R S S, Hammerlindl J K, Pelcher L E, Crosby W L, Selvaraj G (1991) A bifunctional fusion between β-glucoronidase and neomycin phosphotransferase: a broad-spectrum marker enzyme for plants. Gene 101: 239–246

Davin L B, Lewis N G (1992) Phenylpropanoid metabolism: biosynthesis of monolignols, lignans and neolignans, lignins and suberins. In H A Stafford, R K Ibrahim, eds, Phenolic metabolism in plants, Plenum Press, New York, pp 325–375

Dixon R A, Lamb C J, Masoud S, Sewalt V J H, Paiva N L (1996) Metabolic engineering: prospects for crop improvement through the genetic manipulation of phenylpropanoid biosynthesis and defense responses—a review. Gene 179: 61–71

Dixon R A, Steele C L (1999) Flavonoids and isoflavonoids—a gold mine for metabolic engineering. Trends Plant Sci 4: 394–400

Dooner H K, Robbins T P, Jorgensen R A (1991) Genetic and developmental control of anthocyanin biosynthesis. Annu Rev Genet 25: 173–199

Douglas C J (1996) Phenylpropanoid metabolism and lignin biosynthesis: from weeds to trees. Trends Plant Sci 1: 171–178

Dwivedi U N, Campbell W H, Yu J, Datla R S S, Bugos R C, Chiang V L, Podila G K (1994) Modification of lignin biosynthesis in transgenic Nicotiana through expression of an antisense O-methyltransferase gene from Populus. Plant Mol. Biol. 26: 61–71

Ehlting J, Buttner D, Wang Q, Douglas C J, Somssich I E, Kombrink E (1999) Three 4-coumarate:coenzyme ligases in Arabidopsis thaliana represent two evolutionarily divergent classes in angiosperms. Plant Journal 19: 9–20.

Elkind Y, Edwards R, Mavandad M, Hedrick S A, Ribak O, Dixon R A, Lamb C J (1990) Abnormal plant development and down-regulation of phenylpropanoid biosynthesis in transgenic tobacco containing a heterologous phenylalanine ammonia-lyase gene. Proc. Natl. Acad. Sci. 87: 9057–9061

Fenwick G R (1979) A micromethod for the screening of individual seeds and cotyledons of Brassica napus and Brassica campestris (rapeseed) for low sinapine content. J Sci Food Agric 30: 661–663

Harlow, Ed and Lane, D. (1988). Antibodies: A laboratory Manual. 53–138

Halpin C, Knight M E, Foxon G A, Campbell M M, Boudet A M, Boon J J, Chabbert B, Tollier M-T, Schuch W (1994) Manipulation of lignin quality by downregulation of cinnamyl alcohol dehydrogenase. Plant Journal 6: 339–350

Hirji R, Hammerlindl J K, Woytowich A E, Khachatourians G G, Datla R S S, Keller W A Selvaraj G (1996) Plasmid pHS723 and its derivative: plant transformation vectors that enable efficient selection and progeny analysis. Fourth Canadian plant tissue culture and genetic engineering conference, Saskatoon, Saskatchewan, Canada Hu W-J, Kawaoka A, Tsai C-J, Lung J, Osakabe K, Ebinuma H, Chiang V L (1998) Compartmentalized expression of two structurally and functionally distinct 4-coumarate:CoA ligase genes in aspen (*Populus tremuloides*). Proc Natl Acad Sci USA 95: 5407–5412

Humphreys J M, Hemm M R, Chapple C (1999) New routes for lignin biosynthesis defined by biochemical characterization of recombinant ferulate 5-hydroxylase, a multifunctional cytochrome P450-dependent monooxygenase. Proc Natl Acad Sci USA 96: 10045–10050

Inoue K, Sewalt V J H, Murray Ballance G, Ni W, Sturzer C, Dixon R A (1998) Developmental expression and substrate specificities of Alfalfa caffeic acid 3-O-methyltransferase and caffeoyl coenzyme A 3-O-methyltransferase in relation to lignification. Plant Physiol 117: 761–770

Ismail F, Vaisey-Genser M, Fyfe B (1981) Bitterness and astringency of sinapine and its components. J Food Sci 46: 1241–1244

Jefferson R A, Burgess S M, Hirsch D (1986) β-glucoronidase from *Escherchia coli* as a gene-fusion marker. Proc Natl Acad Sci USA 83: 8447–8451

Joseffson L G, Lenman M, Ericson M L, Rask L (1987) Structure of a gene encoding the 1.7S storage protein, napin, from *Brassica napus*. J Biol Chem 262: 12196–12201

Joshi C P, Zhou H, Huang X, Chiang V L (1997) Context sequences of translation initiation codon in plants. Plant Mol Biol 35: 993–1001

Kajita S, Hishiyama S, Tomimura Y, Katayama Y, Omori S (1997) Structural changes of modified lignin in transgenic tobacco plants in which the activity of 4-coumarate Coenzyme A ligase is depressed. Plant Physiol. 114: 871–879

Keith Lindsey (1998) Transgenic Plant Research. Harwood Academic Publishers, Australia. pp: 1–55.)

Kianian SF, Quiros CF (1992) Generation of a *Brassica oleracea* composite RFLP map: Linkage arrangements among various populations and evolutionary implications. Theor Appl Genet 84: 544–554

Kohno-Murase J, Murase M, Ichikawa H, Imamura J (1994) Effects of an antisense napin gene on seed storage compounds in transgenic *Brassica napus* seeds. Plant Mol Biol 26:1115–1124

Koncz C, Schell J (1986) The promoter of $T_L$-DNA gene 5 controls the tissue-specific expression of chimaeric genes carried by a novel type of Agrobacterium binary vector. Mol Gen Genet 204: 383–396

Kozak, M. (1987). An analysis of 5'-noncoding sequences from 699 vertebrate messenger RNAs. Nucleic Acids Res. 15: 8125–8148

Lee D Douglas CJ (1996) Two divergent members of a tobacco 4-Coumarate:coenzyme A ligase (4cl) gene family. cDNA structure, gene inheritance and expression, and properties of recombinant proteins. Plant Physiol 112: 193–205

Lee D, Ellard M, Wanner L A, Davis K R, Douglas C J (1995) The *Arabidopsis thaliana* 4-coumarate:CoA ligase (4CL) gene: stress and developmentally regulated expression and nucleotide sequence of its cDNA. Plant Mol Biol 28: 871–884

Lee D, Meyer K, Chapple C, Douglas C J (1997) Antisense suppression of 4coumarate:coenzyme A ligase activity in Arabidopsis leads to altered lignin subunit composition. Plant Cell 9: 1985–1998.

Lewis N G, Yamamoto E (1990) Lignin: Occurrence, biogenesis and biodegradation. Ann Rev Plant Physiol Plant Mol Biol 41: 455–496

Lindberg R L P, Negishi M (1989) Alteration of mouse cytochrome p450coh substrate specificity by mutation of a single amino-acid residue. Nature 339: 632–634.

Mackay J J, O'Malley D M, Presnell T, Booker F L, Campbell M M, Whetten R W, Sederoff R R (1997) Inheritance, gene expression, and lignin characterization in a mutant pine deficient in cinnamyl alcohol dehydrogenase. Proc. Natl. Acad. Sci. 94: 8255–8260

Marita J M, Ralph J, Hatfield R D, and Chapple C (1999) NMR characterization of lignins in Arabidopsis altered in the activity of ferulate 5-hydroxylase. Proc Natl Acad Sci 96: 12328–12332.

Meyer K, Cusumano J C, Somerville C, Chapple C C S (1996) Ferulate-5-hydroxylase from *Arabidopsis thaliana* defmes a new family of cytochrome P450-dependent monooxygenases. Proc Natl Acad Sci USA 93: 6869–6874

Meyer K, Shirley A M, Cusumano J C, Bell-Lelong D A, Chapple C (1998) Lignin monomer composition is determined by the expression of a cytochrome P450-dependent monooxygenase in Arabidopsis. Proc Natl Acad Sci USA 95: 6619–6623.

Mizutani M, Ohta D, Sato R (1997) Isolation of a cDNA and a genomic clone encoding cinnamate 4-hydroxylase from Arabidopsis and its expression manner in planta. Plant Physiol 113: 755–763

Mol J N M, Blokland R V, Lange P D, Stam M, Kooter J M (1994) Post-transcriptional inhibition of gene expression: sense and antisense genes. In Paszkowski J, ed, Homologous recombination and gene silencing in plants. Kluwer Academic Publishers, Netherlands, 309–333

Mol J, Grotewold E, Koes R (1998) How genes paint flowers and seeds. Trends Plant Sci 3: 212–217

Moloney M M, Walker J M, Sharma K K (1989) High efficiency transformation of *Brassica napus* using Agrobacterium vectors. Plant Cell Reports 8: 238–242

Ni W, Paiva N L, Dixon R A (1994) Reduced lignin in transgenic plants containing a caffeic acid O-methyltransferase antisense gene. Transgenic Research 3: 120–126

Osakabe K, Tsao C C, Li L, Popko J L, Umezawa T, Carraway D T, Smeltzer R H, Joshi C P, Chiang V L (1999) Coniferyl aldehyde 5-hydroxylation and methylation direct syringyl lignin biosynthesis in angiosperms. Proc Natl Acad Sci USA 96: 8955–8960

Pearson A W, Butler E J, Fenwick R G (1980) Rapeseed meal and egg taint: The role of sinapine. J Sci Food Agric 31: 898–904

Regenbrecht J, Strack D (1985) Distribution of 1-sinapoylglucose:choline sinapoyltransferase activity in the brassicaceae. Phytochemistry 24: 407–410

Ruegger M, Meyer K, Cusumano J C, Chapple C (1999) Regulation of ferulate-5-hydroxylase expression in Arabidopsis in the context of sinapate ester biosynthesis. Plant Physiology 119: 101–110

Sambrook J, Fritisch E F, Maniatis T (1989) Molecular cloning: A laboratory manual. Cold Spring Harbor Laboratory Press, New York.

Schmid J, Doerner P W, Clouse S D, Dixon R A, Lamb C J (1990) Developmental and environmental regulation of a bean chalcone synthase promoter in transgenic tobacco. Plant Cell 2: 619–631

Siciliano S D, Theoret C M, de Freitas J R, Hucl P J, Germida J J (1998) Differences in the microbial communities associated with the roots of different cultivars of canola and wheat. Can J Microbiol 44: 844–851

Slocombe S P, Piffanelli P, Fairbairn D, Bowra S, Hatzopoulos P, Tsiantis M, Murphy D J (1994) Temporal and tissue-specific regulation of a *Brassica napus* stearoyl-acyl carrier protein de-saturase gene. Plant Physiol 103: 1167–1176

Strack D (1981) Sinapine as a supply of choline for the biosynthesis of phosphatidylcholine in Raphanus sativus seedlings. Z Naturforsch 36c: 215–221

Strack D (1997) Phenolic metabolism. In P B Dey, J B Harborne, eds, Plant Biochemistry, Academic Press, Toronto, pp 387416

Strack D, Ellis B E, Graewe W, Heilemann J (1990) Sinapoylglucose: Malate sinapoyltransferase activity in seeds and seedlings of rape. Planta 180: 217–219

Temple S J, Knight T J, Unkefer P J, Sengupta-Gopalan C (1993) Modulation of glutamine synthetase gene expression in tobacco by the introduction of an alfalfa glutamine synthetase gene in sense and antisense orientation: molecular and biochemical analysis. Mol Gen Genet 236: 315–323

Truco M J, Hu J, Sadowski J, Quiros C F (1996) Inter- and Intra-genomic homology of the Brassica genomes: Implications for their origin and evolution. Theor Appl Genet 93: 1225–1233.

Tsai C-J, Popko J L, Mielke M R, Hu W-J, Podila G K, Chiang V L (1998) Suppression of O-methyltransferase gene by homologous sense transgene in quaking aspen caused red-brown wood phenotypes. Plant Physiol. 117: 101–112

Velasco L, Mollers C (1998) Nondestructive assessment of sinapic acid esters in Brassica species: II. Evaluation of germplasm and identification of phenotypes with reduced levels. Crop Sci 38: 1650–1654

Vignols F, Rigau J, Torres M A, Capellades M, Puigdomemech P (1995) The brown midrib3 (bm3) mutation in maize occurs in the gene encoding Caffeic acid O-methyltransferase. Plant Cell 7: 407–416

Vogt T, Aebershold R, Ellis B (1993) Purification and characterization of sinapine synthase from seeds of *Brassica napus*. Arch Biochem Biophys 300: 622–628

Wachenfeldt C V, Johnson E F (1995) Structures of eukaryotic cytochrome P450 enzymes. In P R Ortiz de Montellano, ed, Plenum Press, New York, pp 183–223.

Wang S X, Oomah B D, McGregor D I, Downey R K (1998) Genetic and seasonal variation in the sinapine content of seed from Brassica and Sinapis species. Can J Plant Sci 78: 395–400

Wanner L A, Guoqing L, Ware D, Somssich I E, Davis K R (1995) The phenylalanine ammonia-lyase gene family in *Arabidopsis thaliana*. Plant Mol Biol 27: 327–338

Weisshaar B, Jenkins G I (1998) Phenylpropanoid biosynthesis and its regulation. Curr Opin Plant Biol 1: 251–257

Whetten, R. and Sederoff, R. (1995). Lignin Biosynthesis. The Plant Cell 7:1001–1013

Whetten R W, Mackay J J, Sederoff R R (1998) Recent advances in understanding lignin biosynthesis. Annu Rev Plant Physiol Plant Mol Biol 49: 585–609.

The disclosures of the above references are specifically incorporated herein by reference.

What we claim is:

1. A transformed seed-producing plant, or a part thereof, of the Cruciferae family containing an exogenous DNA sequence operably linked to a promoter for expression of a polypeptide that acts as a CYP84 monooxygenase enzyme, or a polypeptide that is an antisense equivalent of a CYP84 monooxygenase enzyme, or a polypeptide that is a catalytic fragment or derivative of the monooxygenase enzyme or antisense equivalent that does not alter the function of the CYP84 enzyme or antisense equivalent, and which plant or plant part has a reduced content of sinapine in seeds thereof compared to vector control plants or plant parts of the same species lacking the exogenous DNA sequence, wherein the exogenous DNA sequence is selected from the group consisting of SEQ ID NO:1, SEQ ID NO:2 and SEQ ID NO:3, or is a sequence complementary to a sequence selected from the group consisting of SEQ ID NO:1, SEQ ID NO:2 and SEQ ID NO:3, or is an analogue, homologue or derivative thereof, or a sequence having at least 40% identity with a sequence selected from the group consisting of SEQ ID NO:1, SEQ ID NO:2 and SEQ ID NO:3, or at least 40% identity with a sequence complementary thereto.

2. An isolated nucleic acid molecule comprising a nucleotide sequence selected from the group consisting of SEQ ID NO:1, SEQ ID NO:3 or SEQ ID NO:5, or an active fragment, derivative, homolog or analog thereof, or a sequence that is complementary to SEQ ID NO:1, SEQ ID NO:3 or SEQ ID NO:5, or an active fragment thereof, derivative, homolog or analog thereof, or a sequence having at least 90% identity to said sequence or complementary sequence.

3. The isolated nucleic acid molecule of claim 2, comprising the sequence of nucleotides of SEQ ID NO:1.

4. The isolated nucleic acid molecule of claim 2, comprising the sequence of nucleotides of SEQ ID NO:3.

5. The isolated nucleic acid molecule of claim 2, comprising the sequence of nucleotides SEQ ID NO:5.

6. The isolated nucleic acid molecule of claim 2, comprising a sequence that is complementary to SEQ ID NO:1.

7. The isolated nucleic acid molecule of claim 2, comprising a sequence of nucleotides that is complementary to SEQ ID NO:3.

8. The isolated nucleic acid molecule of claim 2, comprising a sequence of nucleotides that is complementary to SEQ ID NO:5.

9. A vector for transforming plants of the crucifera family, said vector comprising a promoter, a start codon, a sequence operably linked to said promoter, selected from the group consisting of SEQ ID NO:1, SEQ ID NO:3, and SEQ ID NO:5, or a sequence complementary thereto, or an active fragment, homolog, analog or derivative of said sequence or complementary sequence, and a stop codon.

10. The vector of claim 9, wherein the promoter is the CaMV 35S promoter.

11. The vector of claim 9, wherein the promoter is the napin promoter.

12. Plasmid identified by Accession No. IDAC 020500-5.

13. Plasmid identified by Accession No. IDAC 020500-6.

14. Plasmid identified by Accession No. IDAC 020500-7.

15. A transgenic *Brassica napus* plant, or part thereof, transformed with the vector of claim 9.

16. A chimeric gene causing reduced sinapine content in plant cells of the Crucifera family transformed with the chimeric gene, the chimeric gent comprising:
   a regultory nucleotide sequence; and
   a nucleic acid fragment encoding an active plant CYP84 enzyme having an amino acid sequence selected from the group consisting of SEQ ID NO:2, DSEQ ID NO:4 or SEQ ID NO:6; and
   wherein the nucleic acid fragment is operable linked in either the sense or antisense orientation to the regulatory sequence.

17. The chimeric gene of claim 16 wherein the CYP84 enzyme is a F5H enzyme.

18. The chimeric gene of claim 16 wherein the nucleic acid fragment is operably linked in the sense orientation to said regulatory sequence.

19. The chimeric gene of claim 16 wherein the nucleic acid fragment is operably linked in the antisense orientation to said regulatory sequence.

20. The chimeric gene of claim 16 wherein the regulatory sequence comprises a promoter selected from the group consisting of a napin promoter, a phaseolin promoter, an oleosin promoter and a cruciferin promoter.

21. The chimeric gene of claim 16 wherein the regulatory sequence comprises an endogenous plant promoter effective for controlling expression of a plant CYP84 gene.

* * * * *